United States Patent [19]
Danvy et al.

[11] Patent Number: 5,612,371
[45] Date of Patent: Mar. 18, 1997

[54] AMINO ACID, DERIVATIVES, PROCESSES FOR THEIR PREPARATION AND THEIR THERAPEUTIC APPLICATION

[75] Inventors: Denis Danvy, Yvetot; Thierry Monteil, Mont-Saint-Aignan; Christophe Lusson, Rouen; Jean-Charles Schwartz, Paris; Claude Gros, Paris; Nadine Noel, Paris; Jeanne-Marie Lecomte, Paris; Pierre Duhamel; Lucette Duhamel, both of Mont-Saint-Aignan, all of France

[73] Assignee: Societe Civile Bioproject, Paris, France

[21] Appl. No.: 276,665

[22] Filed: Jul. 18, 1994

[30] Foreign Application Priority Data

Jul. 16, 1993 [FR] France .................... 93 08765

[51] Int. Cl.⁶ ............ A61K 31/36; A61K 31/195; A61K 31/215; C07C 323/29; C07C 327/06; C07C 317/50; C07D 317/50
[52] U.S. Cl. ............ 514/465; 514/469; 514/513; 514/538; 514/562; 549/441; 549/467; 558/254; 560/16; 562/426
[58] Field of Search .................. 558/255, 254; 514/465, 513, 538, 562; 560/16; 562/426; 549/441

[56] References Cited

U.S. PATENT DOCUMENTS 4,401,677  8/1983  Greenberg et al. .
4,722,810  2/1988  Delaney et al. ............ 558/254 X

FOREIGN PATENT DOCUMENTS 038758   4/1981   European Pat. Off. .
136883   9/1984   European Pat. Off. .
419327   9/1989   European Pat. Off. .
2556721  12/1983  France .

Primary Examiner—Johann Richter
Assistant Examiner—Michael G. Ambrose
Attorney, Agent, or Firm—Larson & Taylor

[57] ABSTRACT

New amino acid derivatives, processes for their preparation and their therapeutic application.

Amino acid derivatives corresponding to the general formulae

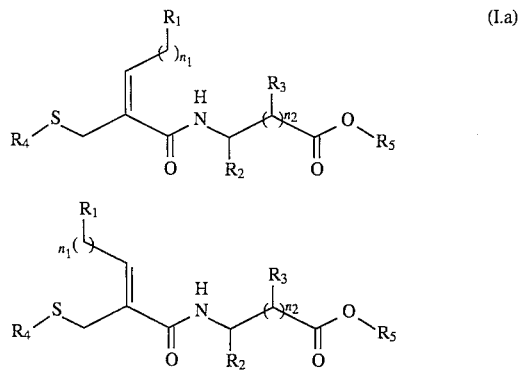

These derivatives may be used as medicaments which exhibit an enkephalinase-inhibitory activity.

5 Claims, No Drawings

AMINO ACID, DERIVATIVES, PROCESSES FOR THEIR PREPARATION AND THEIR THERAPEUTIC APPLICATION

The present invention relates to new amino acid derivatives, to processes for their preparation and to their therapeutic application.

The new derivatives according to the invention are inhibitors of enkephalinase, which is an enzyme which degrades enkephalins.

Methionine-enkephalin and leucine-enkephalin are pentapeptides which have been discovered in the brain and which are endogenous ligands of the morphinic receptor (J. Hughes et al., Nature 258, 577–579 (1975)).

These peptides are considered as neuromediators having inhibitory action on the release of other neuro-transmitters (J. Hughes, Nature 278, 394 (1979); S. H. Snyder, Nature 278, 13 (1979)). It has been demonstrated that enkephalins are rapidly degraded by a carboxydipeptidase ("enkephalinase") which releases Tyr-Gly-Gly and Phe-Met residues (B. Malfroy et al., Nature, 276, p. 523–526 (1978)).

Compounds which are capable of inhibiting enkephalinase may thus prolong the effects of the endogenous enkephalins or may potentiate the action of synthetic analogues administered in an exogenous fashion. These compounds are thus capable of replacing morphinic agents in all their properties without having any of the disadvantages thereof, in particular regarding the phenomena of addiction and dependency.

The development of compounds capable of inhibiting the degradation of the enkephalins by the enzyme enkephalinase has been the subject of extensive research.

By way of illustration of the state of the art, there may be mentioned European Patent Applications 0,038,758 and 0,082,088 (Roques et al.) which describe amino acid derivatives and, more particularly, mercaptoalkanoyl and acylmercaptoalkanoyl amino acid derivatives having an enkephalinase-inhibitory activity.

U.S. Pat. No. 4,401,677 (Greenberg et al.) describes various mercaptoalkanoyl amino acids which are useful as analgesic agents, on account of their enkephalinase-inhibitory activity.

There may also be mentioned European Patent Application No. 0,136,883 (Delaney et al.) which describes enkephalinase inhibitors corresponding to the general formula

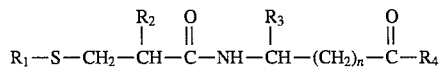

in which $R_1$ represents a hydrogen atom or an acyl group, $R_2$ represents, inter alia, a benzyl radical, the benzene ring being optionally mono- or polysubstituted with a halogen atom, a trifluoromethyl group, a nitro group, a lower alkyl group or a lower alkoxy group, $R_3$ represents, inter alia, a hydrogen atom or a lower alkyl, $R_4$ represents a hydroxyl, esters or amides and n is an integer between 1 and 15.

The new enkephalinase inhibitors in accordance with the invention have the advantage, with respect to the enkephalinase inhibitors known previously, such as those described in the abovementioned patents or patent applications, of lesser bonding to plasma proteins and thus of greater activity, by virtue in particular of the presence in their structure of an ethylenic double bond at the carbon alpha to the carbonyl group of the amide function.

The new amino acid derivatives in accordance with the invention correspond to the general formulae

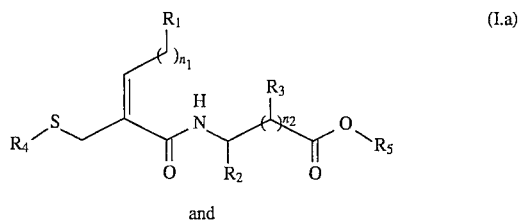

and

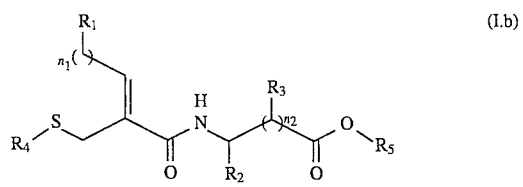

in which $R_1$ represents a hydrogen atom; a phenyl group which is optionally mono- or polysubstituted with a halogen atom, a trifluoromethyl group, a nitro group, a cyano group or an amino group, a lower alkyl group or a lower phenylalkylene group; the group

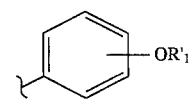

where $R'_1$ represents a hydrogen atom, a lower alkyl group, a phenyl group or a lower phenylalkylene group; a group

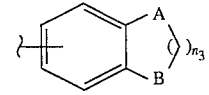

where A, B and $n_3$ have the meanings given below

| A    | B    | $n_3$ |
|------|------|-------|
| O    | O    | 1     |
| O    | CH$_2$ | 1   |
| CH$_2$ | CH$_2$ | 1 |
| O    | O    | 2     |
| CH$_2$ | CH$_2$ | 2 |
| O    | CH$_2$ | 2   | a biphenyl group, alpha and beta naphthyl, $n_1$ varies from 0 to 10

$n_2$ varies from 1 to 10

$R_2$ represents a hydrogen atom; a lower alkyl group; a lower hydroxyalkylene group; a phenyl group; a lower phenylalkylene group; a lower hydroxyphenylalkylene group; a lower aminoalkylene group; a lower guanidinoalkylene group; a lower mercaptoalkylene group; a lower thioalkylene lower alkyl group; a lower imidazolylalkylene group; a lower indolylalkylene group; a lower carbamylalkylene group; a lower carboxyalkylene group;

$R_3$ also represents a hydrogen atom or one of the groups mentioned above for the definition of $R_2$;

$R_4$ represents a hydrogen atom, a linear or branched aliphatic acyl radical, an aromatic acyl radical which is optionally mono- or polysubstituted, or a linear or branched acyl radical containing one or more oxygen atoms;

$R_5$ represents a hydrogen atom; a linear or branched lower alkyl group; a phenyl group or a lower phenylalkylene group, the two last-mentioned groups being optionally mono- or polysubstituted on the phenyl ring; a linear or branched substituent containing one or more oxygen atoms.

Lower alkyl groups is understood to refer to alkyl groups having a linear or branched chain containing 1 to 6 carbon atoms and preferably 1 to 4 carbon atoms.

Lower alkylene groups is understood to refer to alkylene groups containing 1 to 6 carbon atoms and preferably 1 to 4 carbon atoms.

Fluorine is particularly preferred as halogen atom.

Acetyl, propionyl and pivaloyl groups may be mentioned as aliphatic acyl group, the acetyl group being preferred. The benzoyl group may be mentioned as aromatic acyl group.

Among the compounds of formulae (Ia) and (Ib) defined above, one preferred class of compounds comprises the derivatives in which:

$R_1$ represents a phenyl group which is optionally mono- or polysubstituted with a halogen atom or with the trifluoromethyl group, the group

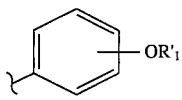

where $R'_1$ represents a lower alkyl group, a phenyl group; the group

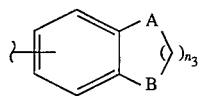

where A and B represent oxygen and $n_3$ is equal to 1 or 2; a biphenyl group, alpha and beta naphthyl;

$R_2$ and $R_3$ represent a hydrogen atom or a lower alkyl radical;

$R_4$ represents a hydrogen atom, a linear or branched aliphatic acyl radical or an aromatic acyl radical;

$R_5$ represents a hydrogen atom, a lower alkyl radical or a phenyl radical;

$n_1$ is equal to 0 or 1;

$n_2$ is equal to 1 or 2.

Among the compounds of formulae (Ia) and (Ib), those which describe the following amino acid structures: beta-alanine and gamma-aminobutyric acid, are preferred.

Among the more particularly preferred compounds of formulae (Ia) and (Ib), there may be mentioned (in the formulae given below, Ph denotes the phenyl group):

1) benzyl N-(E)-[1-oxo-2-(acetylthiomethyl)-3-phenyl-propenyl]-β-alaninate,

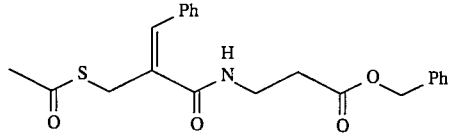

2) methyl N-(E)-[1-oxo-2-(acetylthiomethyl)-3-phenyl-propenyl]-β-alaninate,

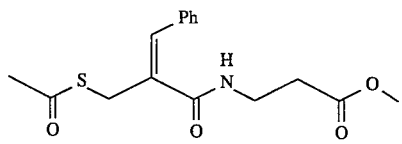

3) ethyl N-(E)-[1-oxo-2-(acetylthiomethyl)-3-phenyl-propenyl]-β-alaninate,

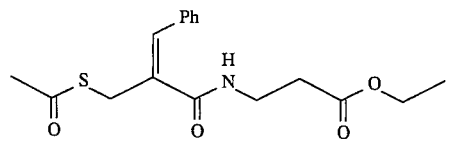

4) N-(E)-[1-oxo-2-(mercaptomethyl)-3-phenylpropenyl]-β-alanine,

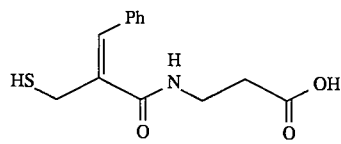

5) benzyl N-(E)-[1-oxo-2-(benzoylthiomethyl)-3-phenyl-propenyl]-β-alaninate,

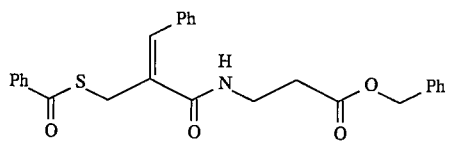

6) methyl N-(E)-[1-oxo-2-(benzoylthiomethyl)-3-phenyl-propenyl]-β-alaninate,

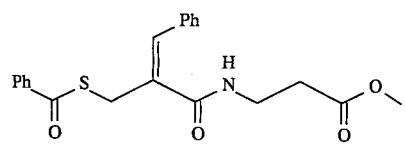

7) ethyl N-(E)-[1-oxo-2-(benzoylthiomethyl)-3-phenyl-propenyl]-β-alaninate,

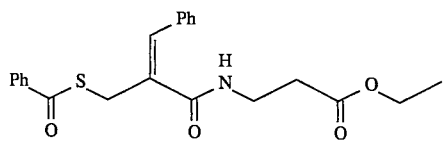

8) benzyl N-(E)-[1-oxo-2-(pivaloylthiomethyl)-3-phenyl-propenyl]-β-alaninate,

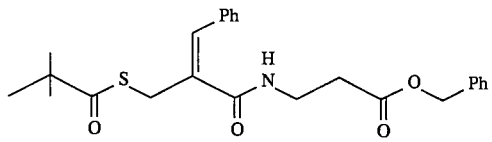

9) methyl N-(E)-[1-oxo-2-(pivaloylthiomethyl)-3-phenyl-propenyl]-β-alaninate,

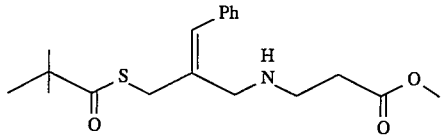

10) ethyl N-(E)-[1-oxo-2-(pivaloylthiomethyl)-3-phenyl-propenyl]-β-alaninate,

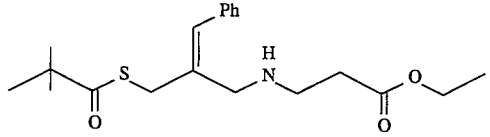

11) methyl 3-(RS)-N-(E)-[1-oxo-2-(acetylthiomethyl)-3-phenylpropenyl] aminobutanoate,

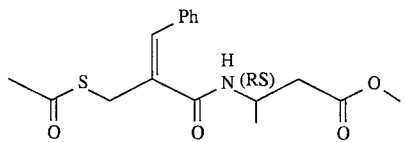

12) 3-(RS)-N-(E)-[1-oxo-2-(mercaptomethyl)-3-phenyl-propenyl]aminobutanoic acid,

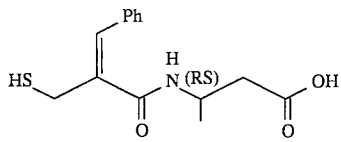

13) methyl 3-(RS)-N-(E)-[1-oxo-2-(acetylthiomethyl)-3-phenylpropenyl]amino-2-methylpropanoate,

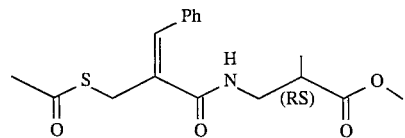

14) 3-(RS)-N-(E)-[1-oxo-2-(mercaptomethyl)-3-phenyl-propenyl]amino-2-methylpropanoic acid,

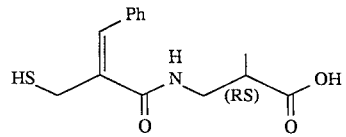

15) benzyl 4-N-(E)-[1-oxo-2-(acetylthiomethyl)-3-phenyl-propenyl]aminobutanoate,

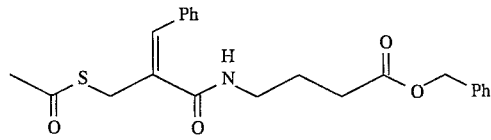

16) 4-N-(E)-[1-oxo-2-(mercaptomethyl)-3-phenylpropenyl]-aminobutanoic acid,

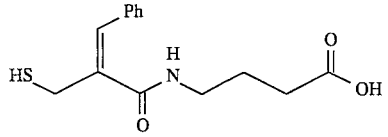

17) benzyl N-(Z)-[1-oxo-2-(acetylthiomethyl)-3-(4-methoxyphenyl)propenyl]-β-alaninate,

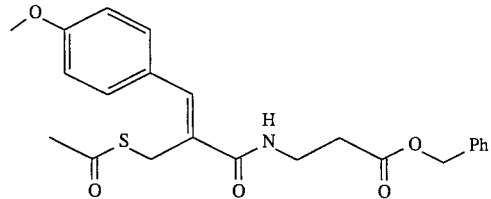

18) benzyl N-(E)-[1-oxo-2-(acetylthiomethyl)-3-(4-methoxyphenyl)propenyl]-β-alaninate,

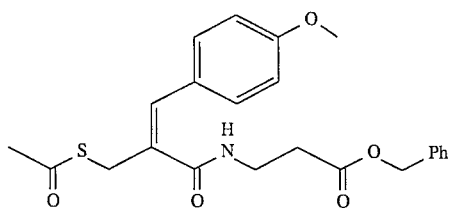

19) N-(E)-[1-oxo-2-(mercaptomethyl)-3-(4-methoxyphenyl)-propenyl]-β-alanine,

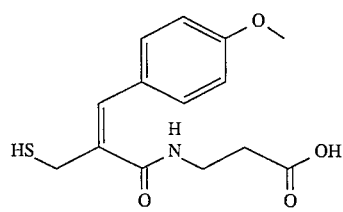

20) benzyl N-(Z)-[1-oxo-2-(acetylthiomethyl)-3-(4-tri-fluoromethylphenyl)propenyl]-β-alaninate,

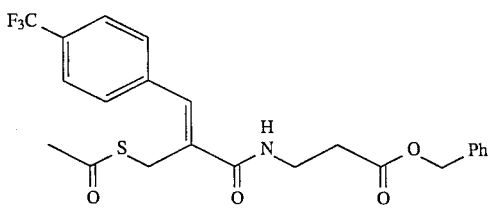

21) benzyl N-(E)-[1-oxo-2-(acetylthiomethyl)-3-(4-tri-fluoromethylphenyl)propenyl]-β-alaninate,

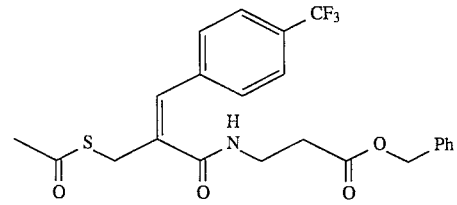

22) N-(E)-[1-oxo-2-(mercaptomethyl)-3-(4-trifluoromethyl-phenyl)propenyl]-β-alanine,

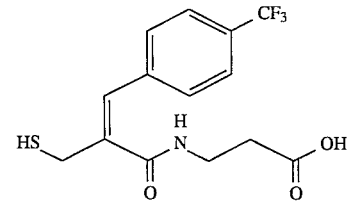

23) benzyl N-(Z)-[1-oxo-2-(acetylthiomethyl)-3-(4-phenylphenyl)propenyl]-β-alaninate,

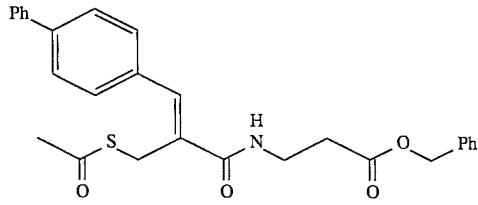

24) benzyl N-(E)-[1-oxo-2-(acetylthiomethyl)-3-(4-phenylphenyl)propenyl]-β-alaninate,

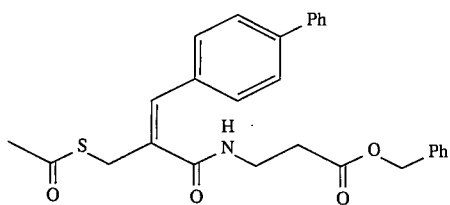

25) N-(E)-[1-oxo-2-(mercaptomethyl)-3-(4-phenylphenyl)-propenyl]-β-alanine,

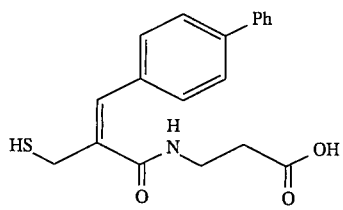

26) benzyl N-(Z)-[1-oxo-2-(acetylthiomethyl)-3-(4-ethoxyphenyl)propenyl]-β-alaninate,

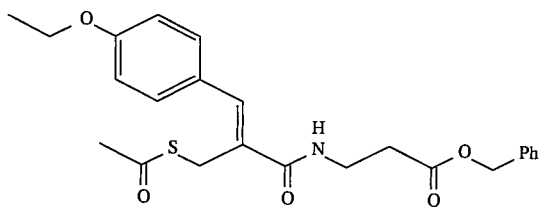

27) benzyl N-(E)-[1-oxo-2-(acetylthiomethyl)-3-(4-ethoxyphenyl)propenyl]-β-alaninate,

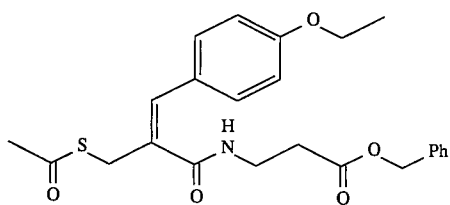

28) N-(E)-[1-oxo-2-(mercaptomethyl)-3-(4-ethoxyphenyl)propenyl]-β-alanine,

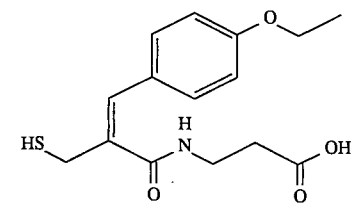

29) benzyl N-(Z)-[1-oxo-2-(acetylthiomethyl)-3-(4-propoxyphenyl)propenyl]-β-alaninate,

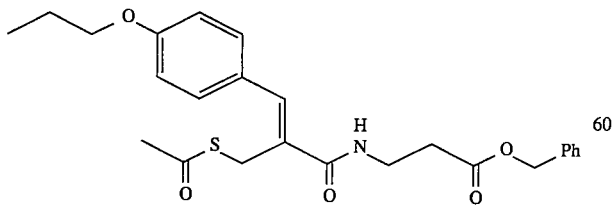

30) benzyl N-(E)-[1-oxo-2-(acetylthiomethyl)-3-(4-propoxyphenyl)propenyl]-β-alaninate,

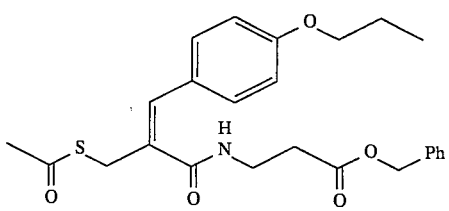

31) benzyl N-(Z)-[1-oxo-2-(acetylthiomethyl)-3-(3,5-difluorophenyl)propenyl]-β-alaninate,

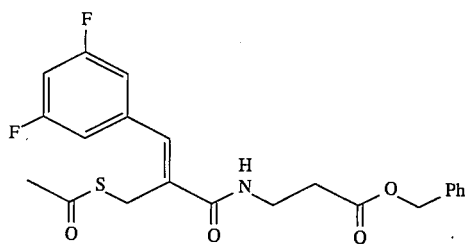

32) benzyl N-(E)-[1-oxo-2-(acetylthiomethyl)-3-(3,5-difluorophenyl)propenyl]-β-alaninate,

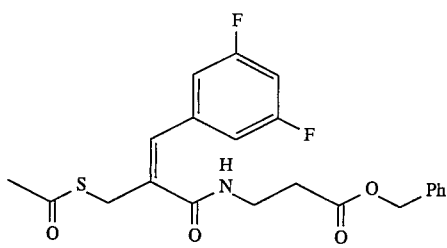

33) N-(E)-[1-oxo-2-(mercaptomethyl)-3-(3,5-difluorophenyl)propenyl]-β-alanine,

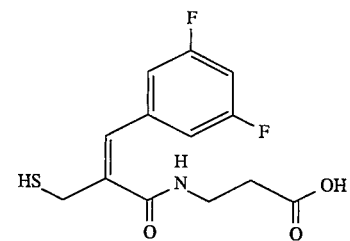

34) benzyl N-(Z)-[1-oxo-2-(acetylthiomethyl)-3-(1-naphthyl)propenyl]-β-alaninate,

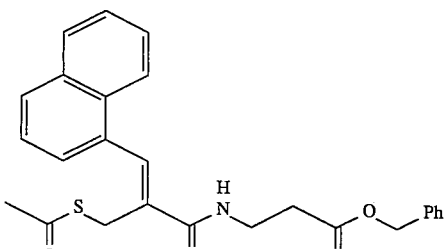

-continued 35) benzyl N-(E)-[1-oxo-2-(acetylthiomethyl)-3-(1-naphthyl)propenyl]-β-alaninate,

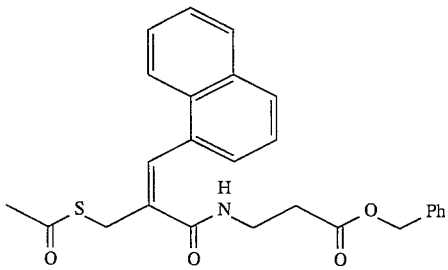

36) N-(E)-[1-oxo-2-(mercaptomethyl)-3-(1-naphthyl)propenyl]-β-alanine,

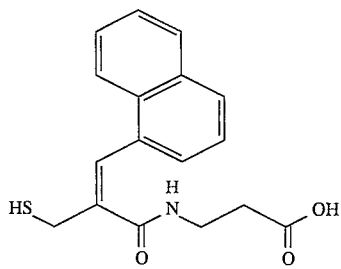

37) benzyl N-(Z)-[1-oxo-2-(acetylthiomethyl)-3-(phenyl)propenyl]-β-alaninate,

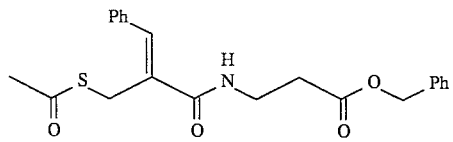

38) N-(Z)-[1-oxo-2-(mercaptomethyl)-3-(phenyl)propenyl]-β-alanine,

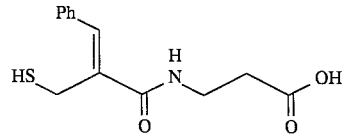

39) benzyl N-(Z)-[1-oxo-2-(acetylthiomethyl)-3-(4-phenoxphenyl)propenyl]-β-alaninate,

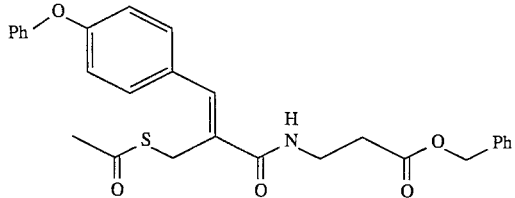

40) benzyl N-(E)-[1-oxo-2-(acetylthiomethyl)-3-(4-phenoxyphenyl)propenyl]-β-alaninate,

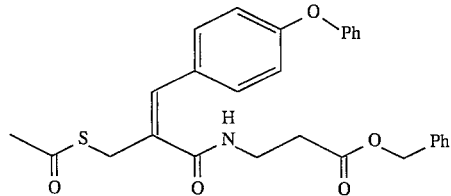

41) N-(E)-[1-oxo-2-(mercaptomethyl)-3-(4-phenoxyphenyl)propenyl]-β-alanine,

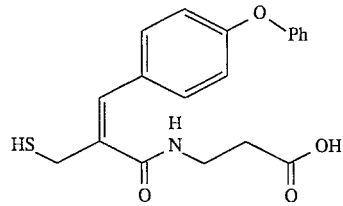

42) benzyl N-(Z)-[1-oxo-2-(acetylthiomethyl)-3-(3,4-methylenedioxyphenyl))propenyl]-β-alaninate,

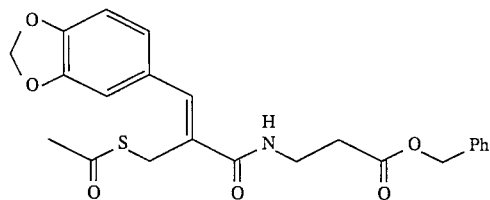

43) benzyl N-(E)-[1-oxo-2-(acetylthiomethyl)-3-(3,4-methylenedioxyphenyl)propenyl]-β-alaninate,

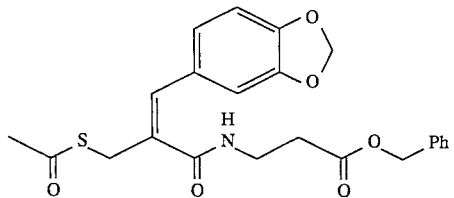

The compounds of formulae (Ia) and (Ib) possess zero, one or two asymmetric centres. They thus exist in racemic mixture form or in optically pure form. All these compounds also enter into the scope of the present invention.

The present invention also relates to the processes for preparing the compounds of formulae (Ia) and (Ib).

The process for preparing the compounds of formula (Ib) (compounds which possess a double bond of (Z) configuration), is characterized in that it consists successively: a) in carrying out an allylic bromination of an ethylenic acid of (E) configuration of formula (II)

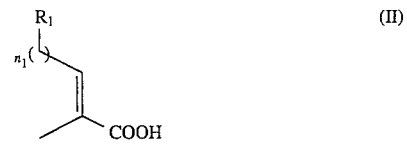

in which $R_1$ has the abovementioned meaning, with a brominating agent such as N-bromosuccinimide in the presence of a catalytic amount of benzoyl peroxide in order to form an acid of formula (III)

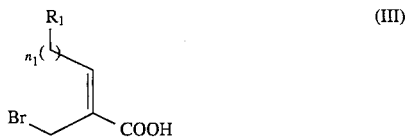

b) in substituting the bromine of the acid of formula (III), preferably with a thioacid $R_4$-SH, in order to form the thioacyl ethylenic acid of (Z) configuration of formula (IV)

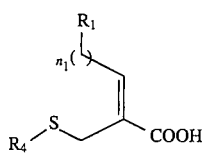

where $R_4$ has the abovementioned definition, c) in coupling the acid of formula (IV) with the desired amino ester salt of formula (V)

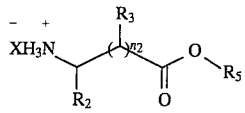

where $R_2$, $R_3$, $R_5$ and $n_2$ have the abovementioned meanings and X represents, for example, halides (in particular chloride), benzenesulphonate, methanesulphonate and toluenesulphonate, in order to form the compound of (Z) configuration of formula (Ib)

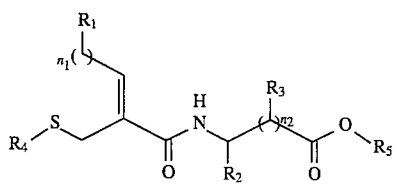

where $R_4$ and $R_5$ are not hydrogen atoms,
d) in subjecting the compound of formula (Ib) to an alkaline deprotection in order to form the compounds of (Z) configuration of formula (Ib) where $R_4$ and $R_5$ are hydrogen atoms

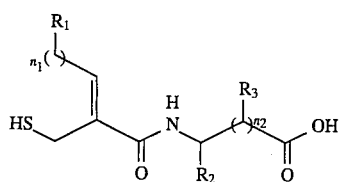

The ethylenic acid of (E) configuration of formula (II) (step a) may be prepared, for example, by a Perkin reaction as described in Org. React. 1, 210–216, 1942.

Substitution of the bromine of the acid of formula (III) with a thioacid (step b) may be carried out according to a method using potassium carbonate and sodium hydrogen carbonate in water or according to a method using diisopropylethylamine in tetrahydrofuran.

The condensation reaction in c) (coupling of the acid of formula (IV) with the amino ester salt of formula (V)) is preferably carried out by using the dicyclohexylcarbodiimide/1-hydroxybenzotriazole (DCC/HOBT) process.

The alkaline deprotection in d) is preferably carried out with aqueous sodium hydroxide solution in methyl alcohol.

The process for preparing the compounds of formula (Ia) (double bond of (E) configuration) is characterized in that it consists successively: a) in isomerizing the ethylenic acid of (Z) configuration of formula (IV)

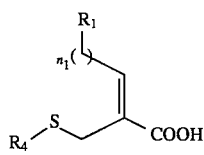

where $R_4$, $R_1$ and $n_1$ have the abovementioned meanings, for example using an ultra-violet (U.V.) lamp, and then in separating the (E/Z) mixture of isomers obtained, by an amine such as cyclohexylamine, in order to obtain the thioacyl ethylenic acid of (E) configuration of formula (VI)

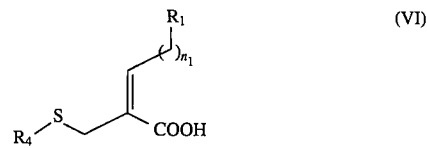

b) in coupling the acid of formula (VI) with the desired amino ester salt of formula (V), in the presence of a coupling agent such as dicyclohexylcarbodiimide, in order to obtain the compound of formula (Ia) of (E) configuration where $R_4$ and $R_5$ are not hydrogen atoms

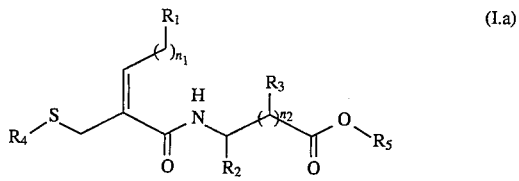

c) and then in subjecting the compound of formula (Ia) to an alkaline deprotection, in order to obtain the compounds of (E) configuration of formula (Ia) where $R_4$ and $R_5$ are hydrogen atoms

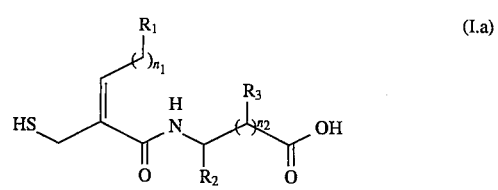

The alkaline deprotection to which the compound of formula (Ia) is subjected is preferably carried out using lithium hydroxide in mixed solvents such as tetrahydrofuran and water.

According to one variant, the compounds of formula (Ia) are prepared: a) by isomerizing the ethylenic acid of formula (IV) possessing a (Z) configuration using an ultra-violet (U.V.) lamp in order to obtain the thioacyl ethylenic acid in the form of a mixture of isomers of (Z/E) configuration of formula (VII)

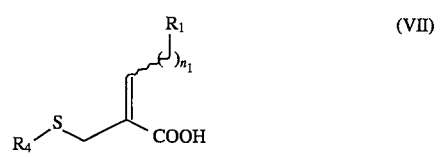

where $R_4$, $R_1$ and $n_1$ have the abovementioned meanings, b) by coupling the acid of formula (VII) with the desired amino ester salt of formula (V) in the presence of a coupling agent such as dicyclohexylcarbodiimide, in order to obtain the compound of formula (VIII) consisting of a (Z/E) mixture of isomers

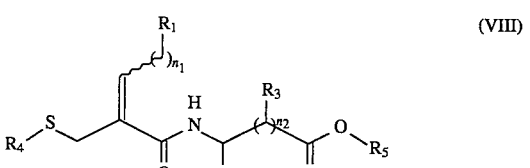

c) by separating the (Z/E) mixture of isomers of the compound of formula (VIII), for example by flash chromatography on silica or by fractional recrystallization, in order to obtain the compound of (E) configuration of formula (Ia) where $R_4$ and $R_5$ are not hydrogen atoms

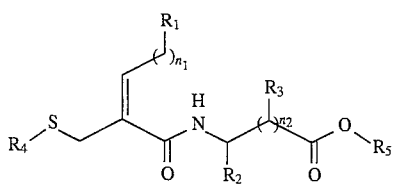

According to another embodiment, the compounds of formula (Ia) where $R_4$ and $R_5$ are not hydrogen, are prepared;
a) by isomerizing the compound of formula (Ib) possessing a double bond of (Z) configuration

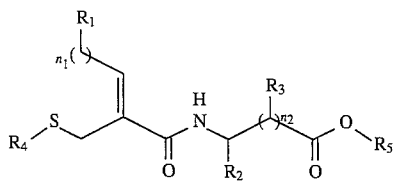

for example using an ultra-violet (U.V.) lamp, preferably in the presence of boron trifluoride etherate, in order to obtain the compound of formula (VIII) consisting of a (Z/E) mixture of isomers

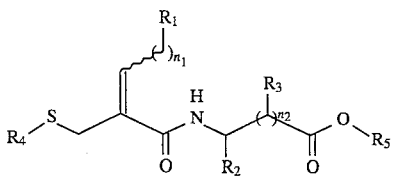

b) by separating the (Z/E) mixture of isomers of the compound of formula (VIII), for example by flash chromatography on silica or by fractional recrystallization, in order to obtain the compound of (E) configuration of formula (Ia) where $R_4$ and $R_5$ are not hydrogen atoms

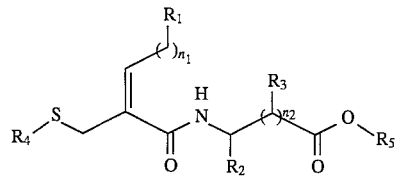

Several examples of implementation of the invention will be given below, in a non-limiting manner. In the examples given below, the following abbreviations have been used for the description of the spectra:

| s: singlet | t: triplet | m: multiplet |
|---|---|---|
| d: doublet | q: quadruplet | app: apparent |

The chemical shifts are expressed in ppm. The melting points are measured on a KOFLER block.

Example 1: Preparation of benzyl N-(E)-[1-oxo-2-(acetylthiomethyl)-3-phenylpropenyl]-β-alaninate A) Preparation of (Z)-2-bromomethyl-3-propenoic acid A mixture of 2 g (12.34 mmol) of (E)-2-methylcinnamic acid, 2.19 g (12.34 mmol) of N-bromosuccinimide (NBS) and a catalytic amount of benzoyl peroxide in 6 ml of $CCl_4$ is heated at reflux for 6 hours. The residue is filtered and washed with ether. The organic phase is washed successively with aqueous 1N HCl solution and then with water. It is dried over $MgSO_4$, filtered and evaporated to dryness. Yield=57% (recrystallized in ether) m.p. 168° C. IR (nujol): 1665 $cm^{-1}$ $^1H$ NMR ($CDCl_3$/TMS): 10.0 (s, 1H); 7.9 (s, 1H); 7.8 to 7.2 (m, 5H); 4.0 (s, 2H).

B) Preparation of (Z)-2-acetylthiomethyl-3-phenylpropenoic acid 2.1 g of the acid obtained above (8.70 mmol), 0.73 g (8.70 mmol) of $NaHCO_3$ and 3 ml of water are mixed. A solution of 0.67 g (8.8 mmol) of thioacetic acid and 1.44 g (10.43 mmol) of $K_2CO_3$ in 21 ml of water is added at 0° C. The mixture is stirred for 15 hours at 20° C. It is acidified with aqueous 6N HCl solution. It is extracted twice with ether. The combined ether phases are washed with water, dried over $MgSO_4$, filtered and concentrated. Yield=67% (recrystallized in ether) m.p. 114° C. IR (nujol): 1670 $cm^{-1}$ $^1H$ NMR ($CDCl_3$/TMS): 9.55 (s, 1H); 8.00 (s, 1H); 7.50 (s, 5H); 4.10 (s, 2H); 2.30 (s, 3H).

C) Preparation of (E)-2-acetylthiomethyl-3-phenylpropenoic acid 2 g of the above (Z) acid dissolved in 30 ml of ethanol are irradiated for 16 hours using a Hanovia TQ 150 lamp. After evaporation, a Z/E acid mixture is obtained in a ratio of 6/4. This mixture is taken up in 25 ml of ether and a solution of 0.39 g of cyclohexylamine (0.4 eq.) in 5 ml of ether is added. After stirring for 30 minutes, the mixture is filtered. The recovered salt is treated with aqueous 3N HCl solution. This is extracted with ether. The organic phase is washed with saturated aqueous NaCl solution, dried over $MgSO_4$, filtered and concentrated. Yield=32% m.p. 57° C. $^1H$ NMR ($CDCl_3$/TMS): 9.60 (s, 1H); 7.30 (s, 5H); 7.20 (s, 1H); 3.85 (s, 2H); 2.25 (s, 3H).

D) Preparation of benzyl N-(E)-[1-oxo-2-(acetylthiomethyl)-3-phenylpropenyl]-β-alaninate 0.95 g (4 mmol) of (E)-2-acetylthiomethyl-3-phenylpropenoic acid dissolved in 15 ml of anhydrous THF is placed in a round-bottomed flask fitted with a calcium chloride guard tube. The flask is cooled to approximately 0°–5° C. in an ice bath and 1.10 g (4 mmol) of benzyl β-alaninate methanesulphonate and 0.41 g (4 mmol) of triethylamine in 5 ml of chloroform, a solution of 0.54 g (4 mmol) of hydroxybenzotriazole monohydrate in 5 ml of THF and a solution of 0.83 g (4 mmol) of dicyclohexylcarbodiimide in 5 ml of chloroform are successively added with stirring. The mixture is allowed to return to room temperature and is stirred for 6 hours.

The precipitate of dicyclohexylurea (DCU) is filtered off and the filtrate is evaporated to dryness. The pasty residue is taken up in ethyl acetate (12 ml). The DCU which has again precipitated is filtered off. The organic phase is washed successively with water (1×10 ml), with saturated aqueous sodium hydrogen carbonate solution (3×10 ml), with water (1×10 ml) and with saturated aqueous NaCl solution (1×10 ml). It is dried over $MgSO_4$, filtered and concentrated. A solid white residue is obtained which is dissolved in the minimum of ether. After recrystallization, 1.25 g of a white solid are obtained. Yield: 78% (recrystallized in ether) m.p. 62° C. IR (nujol): 3220, 1730, 1670, 1650, 1620 $cm^{-1}$ $^1H$ NMR ($CDCl_3$): 7.35 to 7.15 (m, 10H); 6.80 (s, 1H); 5.95 (t, 1H, J=5.1 Hz); 4.95 (s, 2H); 3.85 (d, 2H, J=1 Hz); 3.45 (q app, 2H, J=6.10 Hz); 2.45 (t, 2H, J=6.0 Hz); 2.30 (s, 3H) $^{13}C$ NMR ($CDCl_3$): 194.8; 171.7; 168.2; 135.4; 134.9; 134.2;

132.1; 128.5; 128.3; 128.1; 66.3; 34.5; 33.4; 33.1; 30.5. Microanalysis: $C_{22}H_{23}O_4NS$ Calc. % C=66.48 H=5.83 N=3.52 Found. % C=66.34 H=5.82 N=3.53

Example 2: Preparation of methyl N-(E)-[1-oxo-2-(acetylthiomethyl)-3-phenylpropenyl]-β-alaninate The (E)-2-acetylthiomethyl-3-phenylpropenoic acid described in Example 1 (step C) is coupled with methyl β-alaninate according to the experimental procedure described in Example 1 (step D). Yield: 60% (after flash chromatography, eluent: ether/petroleum ether 6/4) m.p. 54° C. IR (nujol): 3280, 1720, 1680, 1630, 1610 $cm^{-1}$ $^1H$ NMR: 7.20, (s, 5H); 6.80 (s, 1H); 5.90 (broad s, 1H); 3.85 (s, 2H); 3.50 (s, 3H); 3.60 to 3.30 (m, 2H); 2.35 (t, 2H, J=5.30 Hz); 2.25 (s, 3H). Microanalysis: $C_{16}H_{19}O_4NS$ Calc. % C=59.79 H=5.96 N=4.36 Found. % C=59.67 H=6.28 N=4.47

Example 3: Preparation of ethyl N-(E)-[1-oxo-2-(acetylthiomethyl)-3-phenylpropenyl]-β-alaninate The (E)-2-acetylthiomethyl-3-phenylpropenoic acid described in Example 1 (step C) is coupled with ethyl β-alaninate according to the experimental procedure described in Example 1 (step D). Yield=68% (chromatography on silica, eluent: ether/petroleum ether 6/4) m.p.<50° C. IR (nujol): 3300, 1730, 1690, 1640, 1610 $cm^{-1}$ $^1H$ NMR: ($CDCl_3$/TMS)=7.20, (s, 5H); 6.75 (s, 1H); 6.00 (broad s, 1H); 3.95 (q, 2H, J=6, 7 Hz); 3.85 (s, 2H); 3.40 (q app., 2H, J app.=6.2 Hz); 2.30 (t, 2H, J=6.7 Hz); 2.30 (s, 3H); 1.15 (t, 3H, J=6.7 Hz). Microanalysis: $C_{17}H_{21}O_4NS$ Calc. % C=60.87 H=6.31 N=4.18 Found. % C=60.12 H=6.22 N=3.92

Example 4: Preparation of N-(E)-[1-oxo-2-(mercaptomethyl)-3-phenylpropenyl]-β-alanine To a solution of 2 mmol of the diester obtained in Example 1 (step D) dissolved in a THF/$H_2O$ (75/25) mixture, are added, at 0° C. and under an argon atmosphere, 8 mmol of LiOH with stirring for 2 hours. The THF is evaporated off and the aqueous phase is washed with ether and acidified with aqueous 3N HCl solution. It is extracted with ether and the ether extract is washed with saturated aqueous NaCl solution and dried over $MgSO_4$. It is filtered and evaporated. Yield: 63% (after flash chromatography, eluent: ether) m.p. 80° C. IR (nujol): 3340, 1700, 1630, 1610 $cm^{-1}$. $^1H$ NMR (acetone D6): 10.90 to 10.60 (m, 1H); 7.65 (m, 1H); 7.45 to 7.35 (m, 5H); 7.20 (s, 1H); 3.75 to 3.50 (m, 4H); 2.60 (t, 2H, J=6.75 Hz); 2.30 (t, 1H, J=7.50 Hz) Microanalysis: $C_{13}H_{15}O_3NS$ Calc. % C=58.85 H=5.70 N=5.28 Found. % C=58.68 H=5.78 N=5.17

Example 5: Preparation of benzyl N-(E)-[1-oxo-2-(benzoylthiomethyl)-3-phenylropenyl]-β-alaninate

A) Preparation of (Z)-2-benzoylthiomethyl-3-phenylpropenoic acid

The (Z)-2-bromomethyl-3-phenylpropenoic acid described in Example 1 (step A) is reacted with thiobenzoic acid according to the experimental procedure described in Example 1 (step B). Yield=67% (recrystallized in ether) m.p. 160° C. $^1H$ NMR $CDCl_3$/TMS): 8.15 to 7.80 (m, 3H); 7.70 to 7.20 (m, 8H); 4.20 (s, 2H)

B) Preparation of the (Z/E) mixture of 2-benzoylthiomethyl-3-phenylpropenoic acid 2 g of the above (Z) acid dissolved in 20 ml of ethanol are irradiated for 16 hours using a Hanovia TQ 150 lamp. After evaporation, a Z/E acid mixture (60/40) is obtained. $^1H$ NMR ($CDCl_3$/TMS): 9.00 (s, 1H); 8.20 to 6.8 (m, 11H); 4.25 (S, 1.2H); 4.10 (s, 0.8H).

C) Preparation of benzyl N-(E)-[1-oxo-2-(benzoylthiomethyl)-3-phenylpropenyl]-β-alaninate The (Z/E)-2-benzoylthiomethyl-3-phenylpropenoic acid described in Example 5 (step B) is coupled with benzyl β-alaninate according to the experimental procedure described in Example 1 (step D). The (E) isomer is subsequently purified by flash chromatography using the mixture ether/petroleum ether (50/50) as eluent. Yield: 16% m.p. 60° C. IR (nujol): 3320, 1720, 1650, 1620 $cm^{-1}$ $^1H$ NMR ($CDCl_3$/TMS)=8.05 to 7.80 (m, 2H); 7.60 to 7.00 (m, H), 6.90 (s, 1H), 6.00 (broad t, 1H, J=6.2 Hz); 4.90 (s, 2H); 4.05 (s, 2H); 3.4 (q app, 2H, J app.=6.7 Hz); 2.40 (t, 2H, J=5.3 Hz). Microanalysis: $C_{27}H_{25}O_4NS$ Calc. % C=70.57 H=5.48 N=3.05 Found. % C=70.18 H=5.63 N=2.86

Example 6: Preparation of methyl N-(E)-[1-oxo-2-(benzoylthiomethyl)-3-phenylpropenyl]-β-alaninate The (Z/E)-2-benzoylthiomethyl-3-phenylpropenoic acid described in Example 5 (step B) is coupled with methyl β-alaninate according to the experimental procedure described in Example 1 (step D). The (E) isomer is subsequently purified by flash chromatography with the mixture ether/petroleum ether (60/40) as eluent. Yield=16% m.p. 66° C. IR (nujol): 3280, 1730, 1640, 1620 $cm^{-1}$ $^1H$ NMR ($CDCl_3$): 8.10 to 7.80 (m, 2H); 7.70 to 7.10 (m, 8H); 6.90 (s, 1H); 6.00 (broad t, 1H); 4.05 (s, 2H); 3.70 to 3.10 (m, 2H); 3.40 (s, 3H); 2.35 (t, 2H, J=5.4 Hz). Microanalysis: $C_{21}H_{21}O_4NS$ Calc. % C=65.78 H=5.52 N=3.65 Found. % C=65.51 H=5.75 N=3.20

Example 7: Preparation of ethyl N-(E)-[1-oxo-2(benzoylthiomethyl)-3-phenylpropenyl]-β-alaninate The (Z/E)-2-benzoylthiomethyl-3-phenylpropenoic acid described in Example 5 (step B) is coupled with ethyl β-alaninate according to the experimental procedure described in Example 1 (step D). The (E) isomer is subsequently purified by flash chromatography with the mixture ether/petroleum ether (60/40) as eluent. Yield=13% m.p.<50° C. $^1H$ NMR ($CDCl_3$): 8.10 to 7.80 (m, 2H); 7.70 to 7.10 (m, 8H); 6.90 (s, 1H); 6.00 (broad t, 1H); 4.05 (s, 2H); 3.90 (q, 2H, J=7.5 Hz); 3.45 (q app, 2H, J app=5.3 Hz); 2.35 (t, 2H, J=5.3 Hz); 1.10 (t, 3H, J=7.5 Hz) Microanalysis: $C_{22}H_{23}O_4NS$ Calc. % C=66.48 H=5.83 N=3.52 Found. % C=66.80 H=5.92 N=3.75

Example 8: Preparation of benzyl N-(E)-[1-oxo-2-(pivaloylthiomethyl)-3-phenylpropenyl]-β-alaninate

A) Preparation of (Z)-2-pivaloylthiomethyl-3-phenylpropenoic acid

The (Z)-2-bromomethyl-3-phenylpropenoic acid described in Example 1 (step A) is reacted with thiopivaloic acid according to the experimental procedure described in Example 1 (step B). Yield: 93% $^1H$ NMR ($CDCl_3$): 9.10 (broad s, 1H); 7.90 (s, 1H); 7.35 (s, 5H); 4.00 (s, 2H); 1.20 (s, 9H)

B) Preparation of (E)-2-pivaloylthiomethyl-3-phenylpropenoic acid

The (Z)-2-pivaloylthiomethyl-3-phenylpropenoic acid above is irradiated according to the experimental procedure described in Example 1 (step C). Purification of the (E) isomer is carried out according to the experimental procedure described in Example 1 (step C). Yield: 24% (relative to the starting (Z) acid) m.p. 88° C. $^1$H NMR (CDCl$_3$): 8.70 (broad s, 1H); 7.45 to 7.10 (m, 6H); 3.85 (s, 2H); 1.20 (s, 9H).

C) Preparation of benzyl N-(E)-[1-oxo-2-(pivaloylthiomethyl)-3-phenylpropenyl]-β-alaninate The (E)-2-pivaloylthiomethyl-3-phenylpropenoic acid above is coupled with benzyl β-alaninate according to the experimental procedure described in Example 1 (step D). Yield: 63% (after flash chromatography, eluent: ether/petroleum ether 55/45) oil IR: 3320, 1725, 1650, 1620 cm$^{-1}$ $^1$H NMR (CDCl$_3$): 7.30 (s, 5H); 7.20 (s, 5H); 6.75 (s, 1H); 4.90 (s, 2H); 3.80 (s, 2H); 3.45 (q app; 2H, J=6.0 Hz); 2.40 (t, 2H, J=6.5 Hz); 1.20 (s, 9H). Microanalysis: C$_{25}$H$_{29}$NO$_4$S Calc. % C=68.31 H=6.65 N=3.19 Found. % C=68.02 H=6.73 N=3.01

Example 9: Preparation of methyl N-(E)-[1-oxo-2-(pivaloylthiomethyl)-3-phenylpropenyl]-β-alaninate The (E)-2-pivaloylthiomethyl-3-phenylpropenoic acid described in Example 8 (step B) is coupled with methyl β-alaninate according to the experimental procedure described in Example 1 (step D). Yield: 69% (after flash chromatography, eluent: ether/petroleum ether 55/45) oil IR: 3300, 1730, 1660, 1630 cm$^{-1}$ $^1$H NMR (CDCl$_3$): 7.20 (s, 5H); 6.75 (s, 1H); 5.90 (broad t, 1H); 3.80 (s, 2H); 3.50 (s, 3H); 3.60 to 3.25 (m, 2H); 2.40 (t, 2H, J=6.5 Hz); 1.20 (s, 9H) Microanalysis: C$_{19}$H$_{25}$NO$_4$S Calc. % C=62.79 H=6.93 N=3.85 Found. % C=63.20 H=7.10 N=3.92

Example 10: Preparation of ethyl N-(E)-[1-oxo-2-(pivaloylthiomethyl)-3-phenylpropenyl]-β-alaninate The (E)-2-pivaloylthiomethyl-3-phenylpropenoic acid described in Example 8 (step B) is coupled with ethyl β-alaninate according to the experimental procedure described in Example 1 (step D). Yield: 73% (after flash chromatography, eluent: ether/petroleum ether 55/45)–oil IR: 3300, 1710, 1650, 1620 cm$^{-1}$ $^1$H NMR (CDCl$_3$): 7.20 (s, 5H); 6.75 (s, 1H); 6.0 (broad t, 1H); 3.95 (q, 2H, J=7.5 Hz); 3.80 (s, 2H); 3.40 (q app., 2H, J. app=6.40 Hz); 2.35 (t, 2H, J=5.9 Hz); 1.30 to 0.95 (m, 12H). Microanalysis: C$_{20}$H$_{27}$NO$_4$S Calc. % C=63.63 H=7.21 N=3.71 Found. % C=63.35 H=7.16 N=3.52

Example 11: Preparation of methyl 3-(RS)-N-(E)-[1-oxo-2-(acetylthiomethyl)-3-phenylpropenyl)]aminobutanoate The (E)-2-acetylthiomethyl-3-phenylpropenoic acid described in Example 1 (step C) is coupled with methyl 3-(RS)-aminobutanoate according to the experimental procedure described in Example 1 (step D). Yield: 70% (recrystallized) m.p. 98° C. IR (nujol): 3300, 1730, 1700, 1620 cm$^{-1}$ $^1$H NMR (CDCl$_3$): 7.20 (s, 5H); 6.80 (s, 1H); 5.90 (broad d, 1H); 4.50 to 4.10 (m, 1H); 3.85 (s, 2H); 3.50 (s, 3H); 2.30 (s, 5H); 1.00 (d, 3H, J=6.4 Hz). Microanalysis: C$_{17}$H$_{21}$NO$_4$S Calc. % C=60.87 H=6.31 N=4.18 Found. % C=60.34 H=6.27 N=3.98

Example 12: Preparation of 3-(RS)-N-(E)-[1-oxo-2-(mercaptomethyl)-3-phenylpropenyl]aminobutanoic acid Saponification of the above diester is carried out according to the experimental procedure described in Example 4. Yield: 63% (oil) IR: 3280, 1700, 1640, 1600 cm$^{-1}$ $^1$H NMR (CDCl$_3$): 10.0 (s, 1H); 7.20 (s, 5H); 6.65 (s, 1H); 6.15 (d, 1H, J=9.8 Hz); 4.80 to 4.10 (m, 1H); 3.5 (d, 2H, J=8.4 Hz); 2.40 (d, 2H, J=5.6 Hz): 1.75 (t, 1H, J=8.4 Hz); 1.00 (d, 3H, J=7.0 Hz). Microanalysis: C$_{14}$H$_{17}$NO$_3$S Calc. % C=60.19 H=6.13 N=5.01 Found. % C=59.39 H=6.56 N=4.71

Example 13: Preparation of methyl 3-(RS)-N-(E)-[1-oxo-2-(acetylthiomethyl)-3-phenylpropenyl] amino-2-methylpropanoate The (E)-2-acetylthiomethyl-3-phenylpropenoic acid described in Example 1 (step C) is coupled with methyl 3-(RS)-amino-2-methylpropanoate according to the experimental procedure described in Example 1 (step D). Yield: 60% (after flash chromatography), eluent: ether/petroleum ether 6/4) $^1$H NMR (CDCl$_3$): 7.40 to 7.15 (m, 5H); 6.75 (s, 1H); 5.90 (broad t, 1H); 3.85 (s, 2H); 3.55 to 3.35 (m, 1H); 3.50 (s, 3H); 3.25 to 3.05 (m, 1H); 2.65 to 2.45 (m, 1H); 2.35 (s, 3H); 1.05 (d, 3H, J=7.5 Hz) Microanalysis: C$_{17}$H$_{21}$NO$_4$S Calc. % C=60.87 H=6.31 N=4.18 Found. % C=60.53 H=6.28 N=4.30

Example 14: Preparation of 3-(RS)-N-(E)-[1-oxo-2-(mercaptomethyl)-3-phenylpropenyl]amino-2-methylpropanoic acid Saponification of the diester described in Example 13 is carried out according to the experimental procedure described in Example 4. Yield: 60% (after flash chromatography, eluent: ether)–oil $^1$H NMR (CDCl$_3$): 7.40 to 7.10 (m, 6H); 6.85 (broad t, 1H); 6.55 (s, 1H); 3.65 to 3.30 (m, 4H); 2.55 to 2.40 (m, 1H); 1.70 (t, 1H, J=7.5 Hz); 1.05 (d, 3H, J=7.5 Hz) Microanalysis: C$_{14}$H$_{17}$NO$_3$S Calc. % C=60.19 H=6.13 N=5.01 Found. % C=59.48 H=5.99 N=4.79

Example 15: Preparation of benzyl 4-N-(E)-[1-oxo-2-(acetylthiomethyl)-3-phenylpropenyl]aminobutanoate The (E)-2-acetylthiomethyl-3-phenylpropenoic acid described in Example 1 (step C) is coupled with benzyl 4-aminobutanoate according to the experimental procedure described in Example 1 (step D). Yield: 62% (after flash chromatography), eluent: ether/petroleum ether 7/3 ) m.p. 86° C. IR (nujol): 3300, 1720, 1685, 1640, 1610 cm$^{-1}$ $^1$H NMR (CDCl$_3$): 7.45 to 7.15 (m, 10H); 6.80 (s, 1H); 5.55 (broad t, 1H); 5.05 (s, 2H); 3.85 (s, 2H); 3.20 (q. app., 2H, J=6.0 Hz); 2.30 (s, 3H); 2.20 (t, 2H, J=7.5 Hz; 1.75 to 1.50 (m, 2H). Microanalysis: C$_{23}$H$_{25}$NO$_4$S Calc. % C=67.13 H=6.12 N=3.40 Found. % C=67.07 H=6.07 N=3.46

Example 16: Preparation of 4-N-(E)-[1-oxo-2-(mercaptomethyl)-3-phenylpropenyl]aminobutanoic acid Saponification of the diester described in Example 15 is carried out according to the experimental procedure described in Example 4. Yield: 58% (after flash chromatography, eluent: ether)–oil $^1$H NMR (CDC$_{l3}$): 7.4 to 7.10 (m, 6H); 6.65 (s, 1H); 5.70 (broad s, 1H); 3.50 (d, 2H, J=7.5 Hz); 3.25 (q app., 2H, J=6 Hz); 2.20 (t, 2H, J=7.5 Hz); 1.80 to 1.55 (m, 3H). Microanalysis: C$_{14}$H$_{17}$NO$_3$S Calc. % C=60.19 H=6.13 N=5.01 Found. % C=60.60 H=6.32 N=5.31

Example 17: Preparation of benzyl N-(Z)-[1-oxo-2-(acetylthiomethyl)-3-(4-methoxyphenyl)propenyl]-β-alaninate

A) Preparation of (E)-2-methyl-3-(4-methoxyphenyl)propenoic acid

A mixture of 68 g of p-anisaldehyde (500 mmol), 81 g of propionic anhydride (625 mmol) and 48 g of sodium propionate (500 mmol, dried for 5 h at 120° C.) is heated under argon for 30 h at 140° C. This solution, cooled to 80° C., is poured slowly into 400 ml of vigorously stirred saturated aqueous sodium hydrogen carbonate solution. After extraction with dichloromethane (twice 300 ml), the organic phases are combined and then washed with saturated sodium hydrogen carbonate solution (twice 150 ml). The aqueous phases are combined and then poured slowly into a mixture of 300 ml of 12N hydrochloric acid solution and 100 g of crushed ice. The precipitate is collected after filtration, dried in a dessicator, triturated in twice 150 ml of petroleum ether, filtered again and dried in the dessicator. 55.70 g (290 mmol) of a white solid are collected. Yield=58% m.p. 178°–182° C. IR (nujol): 1665 cm$^{-1}$ $^1$H NMR (CDCl$_3$/TMS): 9.20 to 8.90 (broad s, 1H); 7.60 (s, 1H); 7.35 to 6.90) AB, 4H, J=8 Hz); 3.80 (s, 3H); 2.1 (s, 3H) $^{13}$C NMR (CDCl$_3$): 170.40; 158.50, 137.60; 130.90; 128.10; 126.30; 113.50; 54.80.

B) Preparation of (Z)-2-bromomethyl-3-(4-methoxyphenyl)propenoic acid

A mixture of 30 g (156 mmol) of the above acid, 27.80 g (156 mmol) of N-bromosuccinimide (NBS) and a catalytic amount of benzoyl peroxide in 650 ml of CHCl$_3$ is heated at reflux for 6 hours, under irradiation using a halogen lamp (500W). After cooling to room temperature, the solution is washed with 1N hydrochloric acid solution (3 times 200 ml), decanted and then dried over magnesium sulphate, It is filtered, concentrated and triturated twice in 350 ml of an ether/petroleum ether mixture (1/3). The mother-liquors are evaporated and 39.0 g (144 mmol) of a white solid are collected. Yield=92% (after trituration in an ether/petroleum ether mixture 1/2) m.p. 173° C. IR (nujol): 1670 cm$^{-1}$ $^1$H NMR (CDCl$_3$): 9.6 to 9.3 (broad s, 1H); 7.8 (s, 1H); 7.55 and 6.90 (AB, 4H, J=8 Hz); 4.4 (s, 2H); 3.8 (s, 3H)

C) Preparation of (Z)-2-(acetylthiomethyl)-3-(4-methoxyphenyl)propenoic acid To a solution of 8.40 g (31 mmol) of the above acid dissolved in 100 ml of tetrahydrofuran at 0° C. is added dropwise a solution of 4.0 g (31 mmol) of diisopropylethylamine and 2.36 g (31 mmol) of thioacetic acid in 30 ml of tetrahydrofuran. At the end of the addition, the solution is filtered and the filtrate is concentrated. The residue is taken up with 80 ml of dichloromethane and the resulting solution is washed with 60 ml of 1N hydrochloric acid solution. After decantation, the organic phase is dried over magnesium sulphate, filtered and concentrated. 8.09 g (30.4 mmol) of a pale yellow solid are recovered. Yield: 98% m.p. 155° C. IR (nujol): 1690, 1675, 1615 cm$^{-1}$ $^1$H NMR (CDCl$_3$): 10.50 to 10.00 (broad s, 1H); 7.85 (s, 1H); 7.40 and 6.90 (AB, 4H, J=8 Hz); 4.05 (s, 2H); 3.80 (s, 3H); 2.35 (s, 3H).

D) Preparation of benzyl N-(Z)-[1-oxo-2-(acetylthiomethyl)-3-(4-methoxyphenyl)propenyl]-β-alaninate The (Z)-2-acetylthiomethyl-3-(4-methoxyphenyl)propenoic acid obtained in step C is coupled with benzyl β-alaninate according to the experimental procedure described in Example 1 (step D). Yield: 74% (crystallization in a dichloromethane/petroleum ether mixture) m.p. 96° C. IR (nujol): 3280, 1740, 1690, 1640, 1620 cm$^{-1}$ $^1$H NMR (CDCl$_3$/TMS): 7.65 (s, 1H): 7.35 to 7.15 (m, 7H); 6.95 to 6.80 (m, 3H); 5.10 (s, 2H); 4.00 (s, 2H); 3.75 (s, 3H); 3.60 (q, 2H, J app.=6 Hz); 2.60 (t, 2H, J=6 Hz); 2.30 (s, 3H). $^{13}$C NMR (CDCl$_3$): 196.2; 172.0; 167.1; 159.8; 137.9; 135.6; 130.9; 128.5; 128.2; 128.1; 127.2; 114.1; 66.3; 55.2; 35.6; 33.8; 30.2; 26.6. Microanalysis: C$_{23}$H$_{25}$O$_5$NS Calc. % C=64.61 H=5.89 N=3.27 Found. % C=64.20 H=5.73 N=3.48

Example 18: Preparation of benzyl N-(E)-[1-oxo-2-(acetylthiomethyl)-3-(4-methoxylphenyl)propenyl]-β-alaninate 4.93 g (11.5 mmol) of the (Z) diester obtained in Example 17 (step D) are dissolved in 100 ml of methylene chloride which has been passed over basic alumina. The solution is irradiated for 2.5 h using a Hanovia TQ 150 lamp after having added dropwise 1.53 ml of boron trifluoride etherate solution (11.5 mmol). The solution is then washed with 1N hydrochloric acid solution (twice 80 ml), with saturated sodiumhydrogen carbonate solution (twice 80 ml) and is dried over magnesium sulphate. After filtration and evaporation, 2.56 g of (E) isomer are recovered after flash chromatography. Yield=52% (after flash chromatography, eluent: ether/petroleum ether 65/35) m.p.<50° C. IR (nujol): 3290, 1740, 1690, 1630 cm$^{-1}$ $^1$H NMR (CDCl$_3$): 7.35 to 7.05 (m, 7H; 6.75 (AB, 2H, J=8 Hz); 6.70 (s, 1H); 6.10 (t, 1H, J=5 Hz); 4.95 (s, 2H); 3.80 (s, 3H); 3.40 (q app, 2H, J app.=6 Hz); 2.45 (t, 2H, J=6 Hz); 2.25 (s, 3H). $^{13}$C NMR (CDCl$_3$): 194.8; 171.6; 168.6; 159.4; 135.4; 132.0; 131.6; 129.8; 128.5; 128.2; 128.0; 127.2; 113.6; 66.2; 55.0; 34.6; 33.6; 33.2; 30.4 Microanalysis: C$_{23}$H$_{25}$O$_5$NS Calc. % C=64.61 H=5.89 N=3.27 Found. % C=64.17 H=5.91 N=3.48

Example 19: Preparation of N-(E)-[1-oxo-2-(mercaptomethyl)-3-(4-methoxyphenyl)propenyl]-β-alanine Saponification of the (E) diester obtained in Example 18 is carried out according to the experimental procedure described in Example 4. Yield: 69% (after flash chromatography, eluent: ether) m.p. 160° C. IR (nujol): 3340, 1730, 1620, 1580 cm$^{-1}$ $^1$H NMR (CDCl$_3$): 9.10 (broad s, 1H); 7.75 and 7.15 (AB, 4H, J=8Hz); 6.60 (s, 1H); 6.15 (broad t, 1H): 3.75 (s, 3H); 3.50 to 3.45 (m, 4H); 2.50 (t, 2H, J=5 Hz): 1.70 (t; 1H, J=7 Hz). Microanalysis: C$_{14}$H$_{17}$O$_4$NS Calc. % C=56.92 H=5.80 N=4.74 Found. % C=57.11 H=5.86 N=4.91

Example 20: Preparation of benzyl N-(Z)-[1-oxo-2-(acetylthiomethyl)-3-(4-trifluoromethylphenyl)propenyl]-β-alaninate

A) Preparation of (E)-2-methyl-3-(4-trifluoromethylphenyl)propenoic acid

The procedure is performed in an analogous manner to that described in Example 17 (step A), starting from 4-trifluoromethylbenzaldehyde. Yield=88% m.p. 170° C. $^1$H NMR (CDCl$_3$/TMS): 10.55 to 10.00 (broad s, 1H); 7.75 to 7.35 (m, 5H); 2.05 (s, 3H).

B) Preparation of (Z)-2-bromomethyl-3-(4-trifluoromethylphenyl)propenoic acid The procedure is performed in an analogous manner to that described in Example 17 (step B). Yield: 91% m.p. 183° C. IR (nujol): 1665 cm$^{-1}$ $^1$H NMR (CDCl$_3$/TMS): 8.20 to 8.00 (broad s, 1H); 7.80 (s, 1H); 7.70 to 7.55 (m, 4H); 4.30 (s, 2H).

C) Preparation of (Z)-2-(acetylthiomethyl)-3-(4-trifluoromethylphenyl)propenoic acid The procedure is performed in an analogous manner to that described in Example 17 (step C). Yield=82% m.p. 132° C. IR (nujol): 1690, 1670 cm$^{-1}$ $^1$H NMR (CDCl$_3$/TMS): 11.20 to 11.00 (broad s, 1H); 7.90 (s, 1H); 7.70 and 7.50 (AB, 4H, J=10 Hz); 4.05 (s, 2H); 2.35 (s, 3H).

D) Preparation of benzyl N-(Z)-[1-oxo-2-(acetylthiomethyl)-3-(4-trifluoromethylphenyl)propenyl]β-alaninate The (Z)-2-acetylthiomethyl-3-(4-trifluoromethylphenyl)propenoic acid obtained in step C is coupled with benzyl β-alaninate according to the experimental procedure described in Example 1 (step D). Yield=47% (purification by flash chromatography, eluent: ether/petroleum ether 6/4) m.p. 79° C. IR (nujol): 3280, 1740, 1690, 1640, 1620 cm$^{-1}$ $^1$H NMR (CDCl$_3$/TMS): 7.70 (s, 1H); 7.55 (AB, 2H, J=8 Hz); 7.45 to 7.20 (m, 7H); 6.95 (t, 1H, J=6 Hz); 5.15 (s, 2H); 3.90 (s, 2H); 3.40 (q app., 2H, J app.=6 Hz.); 2.65 (t, 2H, J=5 Hz); 2.30 (s, 3H). Microanalysis: C$_{23}$H$_{22}$O$_4$NSF$_3$ Calc. % C=59.35 H=4.76 N=3.01 Found. % C=59.17 H=4.73 N=2.87

Example 21: Preparation of benzyl -(E)-[1-oxo-2-(acetylthiomethyl)-3-(4-trifluoromethylphenyl)propenyl]-β-alaninate The procedure is performed in an analogous manner to that described in Example 18, starting from the (Z) diester obtained in Example 20 (step D). Yield=53% (purification by flash chromatography, eluent: ether/petroleum ether 57/43) m.p. 76° C. IR (nujol): 3290, 1740, 1690, 1630 cm$^{-1}$ $^1$H NMR (CDCl$_3$): 7.45 (AB, 2H, J=8 Hz); 7.35 to 7.20 (m, 7H); 6.70 (s, 1H); 6.25 (t, 1H, J=5 Hz); 3.80 (s, 2H); 3.40 (q. app., 2H, J app.=6 Hz); 2.40 (t, 2H, J=6 Hz); 2.30 (s, 3H). Microanalysis: C$_{23}$H$_{22}$O$_4$NSF$_3$ Calc. % C=59.35 H=4.76 N=3.01 Found. % C=59.01 H=4.51 N=3.24

Example 22: Preparation of N-(E)-[1-oxo-2-(mercaptomethyl)-3-(4-trifluoromethylphenyl)propenyl]-β-alanine Saponification of the (E) diester obtained in Example 21 is carried out according to the experimental procedure described in Example 4. Yield=22% m.p. 108° C. IR (nujol): 1730, 1620, 1580 cm$^{-1}$ $^1$H NMR (CDCl$_3$): 8.50 (broad s, 1H); 7.50 to 7.25 (m, 4H); 6.65 (s, 1H); 6.50 (broad t, 1H); 3.50 to 3.40 (m, 4H); 2.60 (t, 2H, J=6 Hz); 1.80 (t, 1H, J=8 Hz). Microanalysis: C$_{14}$H$_{14}$O$_3$NSF$_3$ Calc. % C=50.45 H=4.23 N=4.20 Found. % C=50.11 H=3.99 N=4.05

Example 23: Preparation of benzyl N-(Z)-[1-oxo-2-(acetylthiomethyl)-3-(4-phenylphenyl)propenyl]-β-alaninate

A) Preparation of (E)-2-methyl-3-(4-phenylphenyl)propenoic acid

The procedure is performed in an analogous manner to that described in Example 17 (step A), starting from 4-phenylbenzaldehyde and using 6 equivalents of propionic anhydride. Yield: 49% m.p. 178° C. IR (nujol): 1670 cm$^{-1}$ $^1$H NMR (CDCl$_3$/TMS): 11.50 to 11.20 (broad s, 1H); 7.70 (s, 1H); 7.60 to 7.20 (m, 9H); 2.15 (s, 3H).

B) Preparation of (Z)-2-bromomethyl-3-(4-phenylphenyl)propenoic acid

The procedure is performed in an analogous manner to that described in Example 17 (step B). Yield: 78% m.p. 16° C. $^1$H NMR (CDCl$_3$/TMS): 7.85 (s, 1H); 7.75 to 7.20 (m, 9H); 7.00 to 6.70 (broad s, 1H); 4.40 (s, 2H).

C) Preparation of (Z)-2-(acetylthiomethyl)-3-(4-phenylphenyl)propenoic acid The procedure is performed in an analogous manner to that described in Example 17 (step C). Yield: 97% m.p. 158° C. IR (nujol)=1690, 1670 cm$^{-1}$ $^1$H NMR (CDC$_3$/TMS): 10.40 to 10.00 (broad s, 1H); 7.95 (s, 1H); 7.75 to 7.20 (m, 9H); 4.15 (s, 2H); 2.35 (s, 3H).

D) Preparation of benzyl N-(Z)-[1-oxo-2-(acetylthiomethyl)-3-(4-phenylphenyl)propenyl]-β-alaninate The (Z)-2-acetylthiomethyl-3-(4-phenylphenyl) propenoic acid obtained in step C is coupled with benzyl β-alaninate according to the experimental procedure described in Example 1 (step D). Yield: 56% (purification by flash chromatography, eluent: ether/petroleum ether 6/4) m.p. 79° C. IR (nujol): 3280, 1740, 1690, 1640, 1620 cm$^{-1}$ $^1$H NMR (CDCl$_3$/TMS): 7.75 (s, 1H); 7.65 to 7.20 (m, 14H); 7.05 (t, 1H, J=5 Hz); 5.0 (s, 2H); 4.15 (s, 2H); 3.65 (q. app., 2H, J app.=6 Hz); 2.65 (t, 2H, J=6Hz); 2.30 (s, 3H). Microanalysis: C$_{28}$H$_{27}$O$_4$NS Calc. % C=71.01 H=5.75 N=2.96 Found. % C=71.08 H=5.60 N=2.46

Example 24: Preparation of benzyl N-(E)-[1-oxo-2-(acetylthiomethyl)-3-(4-phenylphenyl)propenyl]-β-alaninate The procedure is performed in an analogous manner to that described in Example 18, starting from the (Z) diester obtained in Example 23 (step D). Yield=38% (purification by flash chromatography, eluent: ether/petroleum ether 6/4) m.p. 76° C. IR (nujol): 3280, 1740, 1690, 1640, 1620 cm$^{-1}$ $^1$H NMR (CDCl$_3$/TMS): 7.60 to 7.10 (m, 14H); 6.85 (s, 1H); 6.20 to 6.00 (m, 1H); 5.10 (s, 2H); 3.75 (s, 2H); 3.40 (q. app., 2H, J. app.=6 Hz); 2.45 (t, 2H, J=6 Hz); 2.30 (s, 3H). Microanalysis: C$_{28}$H$_{27}$O$_4$NS Calc. % C=71.01 H=5.75 N=2.96 Found. % C=71.29 H=5.51 N=2.75

Example 25: Preparation of N-(E)-[1-oxo-2-(mercaptomethyl)-3-(4-phenylphenyl)propenyl]-β-alanine Saponification of the (E) diester obtained in Example 24 is carried out according to the experimental procedure described in Example 4. Yield: 28% m.p. 125° C. IR (nujol): 1730, 1620, 1580 cm$^{-1}$ $^1$H NMR (CDCl$_3$/TMS): 9.70 (broad s, 1H); 7.70 to 6.80 (m, 11H); 3.80 to 3.40 (m, 4H); 2.50 (t, 2H, J=6 Hz); 1.70 (t, 1H, J=8 Hz). Microanalysis: C$_{19}$H$_{19}$O$_3$NS Calc. % C=66.84 H=5.61 N=4.10 Found. % C=66.45 H=5.29 N=3.79

Example 26: Preparation of benzyl N-(Z)-[1-oxo-2-(acetylthiomethyl)-3-(4-ethoxyphenyl)propenyl]-β-alaninate

A) Preparation of (E)-2-methyl-3-(4-ethoxyphenyl)propenoic acid

The procedure is performed in an analogous manner to that described in Example 17 (step A), starting from 4-ethoxybenzaldehyde. Yield=54% m.p. 180° C. IR (nujol): 1670 cm$^{-1}$ $^1$H NMR (CDCl$_3$/TMS): 7.65 (s, 1H); 7.45 and 6.85 (AB, 4H, J=8 Hz); 6.65 to 6.35 (broad s, 1H); 4.05 (q, 2H, J=6 Hz); 2.05 (s, 3H); 1.30 (t, 3H, J=6 Hz).

B) Preparation of (Z)-2-bromomethyl-3-(4-ethoxyphenyl)propenoic acid

The procedure is performed in an analogous manner to that described in Example 17 (step B). Yield: 45% m.p. 205° C. IR (nujol): 1665 cm$^{-1}$ $^1$H NMR (CDCl$_3$/TMS): 10.40 to 10.00 (broad s, 1H); 7.80 (s, 1H); 7.50 and 6.90 (AB, 4H, J=8 Hz); 4.40 (s, 2H); 4.05 (q, 2H, J=6 Hz); 1.30 (t, 3H, J=6 Hz).

C) Preparation of (Z)-2-(acetylthiomethyl)-3-(4-ethoxyphenyl)propenoic acid The procedure is performed in an analogous manner to that described in Example 17 (step C) Yield: 96% m.p. 145° C. IR (nujol): 1690, 1670 cm$^{-1}$ $^1$H NMR (CDCl$_3$/TMS): 11.00 (s, 1H); 7.85 (s, 1H); 7.40 and 6.95 (AB, 4H, J=8 Hz); 4.25 to 3.90 (m, 4H); 2.35 (s, 3H); 1.35 (t, 3H, J=6 Hz).

D) Preparation of benzyl N-(Z)-[1-oxo-2-(acetylthiomethyl)-3-(4-ethoxyphenyl) propenyl]-β-alaninate The (Z)-2-acetylthiomethyl-3-(4-ethoxyphenyl) propenoic acid obtained in step C is coupled with benzyl alaninate according to the experimental procedure described in Example 1 (step D). Yield=65% (purification by flash chromatography, eluent: ether/petroleum ether 65/35) m.p. 92° C. IR (nujol); 3290, 1740, 1690, 1640, 1620 cm$^{-1}$ $^1$H NMR (CDCl$_3$/TMS): 7.45 (s, 1H); 7.35 to 7.15 (m, 9H); 7.05 to 6.60 (m, 1H); 5.15 (s, 2H); 4.15 to 3.85 (m, 4H); 3.75 to 3.45 (q app., 2H, J app.: 6 Hz); 2.65 (t, 2H, J=7 Hz); 2.30 (s, 3H); 1.35 (t, 3H, J=6 Hz). Microanalysis: C$_{24}$H$_{27}$O$_5$NS Calc. % C=65.29 H=6.16 N=3.17 Found. % C=65.37 H=6.11 N=3.29

Example 27: Preparation of benzyl N-(E)-[1-oxo-2-(acetylthiomethyl)-3-(4-ethoxyphenyl)propenyl]-β-alaninate The procedure is performed in an analogous manner to that described in Example 18, starting from the above (Z) isomer. Yield=42% (after flash chromatography, eluent: ether/petroleum ether 62/38) m.p. 87° C. IR (nujol): 3290, 1740, 1690, 1630 cm$^{-1}$ $^1$H NMR (CDC$_3$/TMS): 7.40 to 7.00 (m, 9H); 6.75 (s, 1H); 6.05 (broad t, 1H); 4.95 (s, 2H); 4.10 to 3.75 (m, 4H); 3.50 (q app., 2H, J app.=6 Hz); 2.60 to 2.20 (M, 5H); 1.30 (t, 3H, J=7 Hz). Microanalysis: C$_{24}$H$_{27}$O$_5$NS Calc. % C=65.29 H=6.16 N=3.17 Found. % C=65.37 H=6.34 N=3.22

Example 28: Preparation of N-(E)-[1-oxo-2-(mercaptomethyl)-3-(4-ethoxyphenyl)propenyl]-β-alanine Saponification of the (E) diester obtained in Example 27 is carried out according to the experimental procedure described in Example 4. Yield: 29% m.p. 148° C. IR (nujol): 1730, 1620, 1580 cm$^{-1}$ $^1$H NMR (CDCl$_3$): 8.30 (broad s, 1H); 7.75 et 7.15 (AB, 4H, J=8 Hz); 6.55 (s, 1H); 6.15 (t, 1H, J=5 Hz); 3.95 (q, 2H, J=6 Hz); 3.50 to 3.45 (m, 4H); 2.50 (t, 2H, J=6 Hz); 1.70 (t, 1H, J=8 Hz); 1.35 (t, 3H, J=6 Hz). Microanalysis: C$_{15}$H$_{19}$O$_4$NS Calc. % C=58.23 H=6.19 N=4.53 Found. % C=58.51 H=6.12 N=4.81

Example 29: Preparation of benzyl N-(Z)-[1-oxo-2-(acetylthiomethyl)-3-(4-propoxyphenyl)propenyl]-β-alaninate

A) Preparation of (E)-2-methyl-3-(4-propoxyphenyl)propenoic acid

The procedure is performed in an analogous manner to that described in Example 17 (step A), starting from 4-propoxybenzaldehyde. Yield=60% m.p. 171° C. IR (nujol): 1665 cm$^{-1}$ $^1$H NMR (CDCl$_3$/TMS): 9.00 to 8.30 (broad s, 1H); 7.75 (s, 1H); 7.35 and 6.90 (AB, 4H, J=8 Hz); 3.95 (t, 2H, J=7 Hz); 2.15 (s, 3H); 1.90 to 1.65 (m, 2H); 1.00 (t, 3H, J=9 Hz).

B) Preparation of (Z)-2-bromomethyl-3-(4-propoxyphenyl)propenoic acid

The procedure is performed in an analogous manner to that described in Example 17 (step B). Yield: 73% m.p. 189° C. IR (nujol): 1670 cm$^{-1}$ $^1$H NMR (CDCl$_3$/TMS): 11.50 to 11.00 (broad s, 1H); 7.80 (s, 1H); 7.40 and 7.00 (AB, 4H, J=8 Hz); 4.40 (s, 2H); 3.90 (t, 2H, J=7 Hz); 1.80 (q. app., 2H, J app.=7 Hz); 1.00 (t, 3H, J=8 Hz).

C) Preparation of (Z) -2-acetylthiomethyl-3-(4-propoxyphenyl)propenoic acid The procedure is performed in an analogous manner to that described in Example 17 (step C). Yield: 98% m.p. 156° C. IR (nujol): 1690, 1675, 1615 cm$^{-1}$ $^1$H NMR (CDCl$_3$/TMS): 8.60 to 8.30 (broad s, 1H); 7.90 (s, 1H); 7.40 and 6.95 (AB, 4H, J=8 Hz); 4.15 (s, 2H); 3.95 (t, 2H, J=7 Hz); 2.35 (s, 3H); 1.80 (q, 2H, J app.=7 Hz); 1.00 (t, 3H, J=8 Hz).

D) Preparation of benzyl N-(Z)-[1-oxo-2-(acetylthiomethyl)-3-(4-propoxyphenyl)propenyl]-β-alaninate The (Z)-2-acetylthiomethyl-3-(4-propoxyphenyl)propenoic acid obtained in step C is coupled with benzyl β-alaninate according to the experimental procedure described in Example 1 (step D). Yield=66% (purification by flash chromatography, eluent: ether/petroleum ether 65/35)–oil IR: 3280, 1740, 1690, 1645, 1620 cm$^{-1}$ $^1$H NMR (CDCl$_3$/TMS): 7.50 (s, 1H); 7.35 to 7.15 (m, 7H); 6.95 to 6.75 (m, 3H); 5.15 (s, 2H); 4.00 to 3.50 (m, 6H); 2.65 (t, 2H, J=6 Hz); 2.30 (s, 3H); 1.80 (m, 2H, J app.=8 Hz); 1.00 (t, 3H, J=8 Hz). Microanalysis: C$_{25}$H$_{29}$O$_5$NS Calc. % C=65.91 H=6.42 N=3.07 Found. % C=65.80 H=6.38 N=2.91

Example 30: Preparation of benzyl N-(E)-[1-oxo-2-(acetylthiomethyl)-3-(4-propoxyphenyl)propenyl]-β-alaninate The procedure is performed in an analogous manner to that described in Example 18, starting from the (Z) isomer. Yield=47% (purification by flash chromatography, eluent: ether/petroleum ether 60/40)–oil IR: 3290, 1740, 1690, 1630 cm$^{-1}$ $^1$H NMR (CDCl$_3$/TMS): 7.55 to 6.65 (m, 10H); 6.15 to 5.85 (m, 1H); 5.00 (s, 2H); 4.05 to 3.35 (m, 6 H); 2.60 to 2.30 (m, 5H); 1.75 (m, 2H, J app.=7 Hz); 0.95 (t, 3H, J=7 Hz). Microanalysis: C$_{25}$H$_{29}$O$_5$NS Calc. % C=65.91 H=6.42 N=3.07 Found. % C=65.90 H=6.53 N=3.21

Example 31: Preparation of benzyl N-(Z)-[1-oxo-2-(acetylthiomethyl)-3-(3,5-difluorophenyl)propenyl]-β-alaninate

A) Preparation of (E)-2-methyl-3-(3,5-difluorophenyl)propenoic acid

The procedure is performed in an analogous manner to that described in Example 17 (step A), starting from 3,5-difluorobenzaldehyde. Yield=82% m.p. 148° C. IR (nujol): 1695, 1620, 1590 cm$^{-1}$ $^1$H NMR (CDCl$_3$/TMS): 11.30 (s, 1H); 7.70 (s, 1H); 7.40 to 6.60 (m, 3H); 2.05 (s, 3H).

B) Preparation of (Z)-2-bromomethyl-3-(3,5-difluorophenyl)propenoic acid

The procedure is performed in an analgous manner to that described in Example 17 (step B). Yield: 63% m.p. 151° C. IR (nujol): 1700, 1620, 1590 cm$^{-1}$ $^1$H NMR (CDCl$_3$/TMS): 8.50 to 8.30 (broad s, 1H); 7.65 (s, 1H); 7.45 to 6.75 (m, 3H); 4.25 (s, 2H).

C) Preparation of (Z)-2-acetylthiomethyl-3-(3,5-difluorophenyl)propenoic acid The procedure is performed in an analgous manner to that described in Example 17 (step C) Yield: 94% m.p. 139° C. IR (nujol): 1700, 1620, 1590 cm$^{-1}$ $^1$H NMR (CDCl$_3$/TMS): 10.35 to 10.15 (broad s, 1H); 7.85 (s, 1H); 7.05 to 6.95 (m, 3H); 4.05 (s, 2H); 2.30 (s, 3H).

D) Preparation of benzyl N-(Z)-[1-oxo-2-(acetylthiomethyl)-3-(3,5-difluorophenyl)propenyl]-β-alaninate The (Z) acid obtained in step C above is coupled with benzyl β-alaninate according to the experimental procedure described in Example 1 (step D). Yield: 54% (after flash chromatography, eluent: ether/petroleum ether 60/40) m.p. 82° C. IR (nujol): 3300, 1750, 1690, 1650 cm$^{-1}$ $^1$H NMR (CDCl$_3$/TMS): 7.40 to 7.05 (m, 6H); 6.95 to 6.70 (m, 4H); 5.15 (s, 2H); 3.90 (s, 2H); 3.65 to 3.45 (m, 2H); 2.65 (t, 2H, J=6 Hz); 2.35 (s, 3H). Microanalysis: C$_{22}$H$_{21}$O$_4$NSF$_2$ Calc. % C=60.96 H=4.88 N=3.23 Found. % C=60.78 H=4.77 N=3.01

Example 32: Preparation of benzyl N-(E)-[1-oxo-2-(acetylthiomethyl)-3-(3,5-difluorophenyl)propenyl]-β-alaninate The procedure is performed in an analogous manner to that described in Example 18, starting from the above (Z) isomer. Yield: 61% (after flash chromatography, eluent: ether/petroleum ether 55/45) m.p. 81° C. IR (nujol): 3300, 1750, 1690, 1640, 1620 cm$^{-1}$ $^1$H NMR (CDCl$_3$): 7.35 to 7.25 (m, 5H); 6.80 (d, 2H, J app.=10 Hz); 6.65 (s, 1H); 6.60 (d, 1H, J app.=10 Hz); 6.10 (t, 1H, J=5 Hz); 5.00 (s, 2H); 3.80 (s, 2H); 3.45 (q, 2H, J app.=6 Hz); 2.50 (t, 2H, J=6 Hz); 2.30 (s, 3H). Microanalysis: C$_{22}$H$_{21}$O$_4$NSF$_2$ Calc. % C=60.96 H=4.88 N=3.23 Found. % C=60.80 H=4.70 N=3.03

Example 33: Preparation of N-(E)-[1-oxo-2-(mercaptomethyl)-3-(3,5-difluorophenyl)propenyl]-β-alanine Saponification of the (E) diester obtained in Example 32 is carried out according to the experimental procedure described in Example 4. Yield: 27% m.p. 125° C. IR (nujol): 1725, 1630, 1580 cm$^{-1}$ $^1$H NMR (CDC$_3$): 9.40 (broad s, 1H); 6.80 to 6.65 (m, 3H); 6.55 (s, 1H); 6.15 (broad t, 1H); 3.55 to 3.40 (m, 4H); 2.50 (t, 2H, J=5 Hz); 1.70 (t, 1H, J=8 Hz). Microanalysis: C$_{13}$H$_{13}$O$_3$NSF$_2$ Calc. % C=51.82 H=4.35 N=4.65 Found. % C=52.11 H=4.26 N=4.42

Example 34: Preparation of benzyl N-(Z)-[1-oxo-2-(acetylthiomethyl)-3-(1-naphphyl)propenyl]-β-alaninate

A) Preparation of (E)-2-methyl-3-(1naphthyl)propenoic acid

The procedure is performed in an analogous manner to that described in Example 17 (step A), starting from 1-naphthaldehyde. Yield: 65% m.p. 155° C. IR (nujol): 1670 cm$^{-1}$ $^1$H NMR (CDCl$_3$/TMS): 11.40 to 10.80 (broad s, 1H); 8.20 (s, 1H); 8.00 to 7.70 (m, 3H); 7.65 to 7.20 (m, 4H); 2.00 (s, 3H).

B) Preparation of (Z)-2-bromomethyl-3-(1-naphthyl)propenoic acid

The procedure is performed in an analogous manner to that described in Example 17 (step B). Yield: 50% m.p. 216° C. IR (nujol): 1670 cm$^{-1}$ $^1$H NMR (CDCl$_3$/TMS): 8.30 (s, 1H); 8.05 to 7.80 (m, 3H); 7.75 to 7.40 (m, 4H); 6.30 to 5.80 (broad s, 1H); 4.30 (s, 2H).

C) Preparation of (Z)-2-acetylthiomethyl-3-(1-naphthyl)propenoic acid

The procedure is performed in an analogous manner to that described in Example 17 (step C). Yield=97% m.p. 175° C. IR (nujol): 1690, 1670 cm$^{-1}$ $^1$H NMR (CDCl$_3$/TMS): 10.40 to 10.00 (broad s, 1H); 7.95 (s, 1H); 7.75 to 7.20 (m, 9H); 4.15 (s, 2H); 2.35 (s, 3H).

D) Preparation of benzyl N-(Z)-[1-oxo-2-(acetylthiomethyl)-3-(1-naphthyl)propenyl]-β-alaninate The above (Z) acid is coupled with benzyl β-alaninate according to the experimental procedure described in Example 1 (step D). Yield: 57% (after flash chromatography, eluent ether/petroleum ether 60/40). m.p. 81° C. IR (nujol): 3290, 1740, 1695, 1640, 1620 cm$^{-1}$ $^1$H NMR (CDCl$_3$/TMS): 8.20 (s, 1H); 8.00 to 7.70 (m, 3H); 7.65 to 7.00 (m, 10H); 5.20 (s, 2H); 3.90 (s, 2H); 3.65 to 3.45 (m, 2H); 2.65 (t, 2H, J=6 Hz); 2.35 (s, 3H). Microanalysis: C$_{26}$H$_{25}$O$_4$NS Calc. % C=69.78 H=5.63 N=3.13 Found. % C=69.86 H=5.68 N=3.17

Example 35: Preparation of benzyl N-(E)-[1-oxo-2-(acetylthiomethyl)-3-(1-naphthyl)propenyl]-β-alaninate The procedure is performed in an analogous manner to that described in Example 18, starting from the (Z) isomer. Yield: 51% (after flash chromatography, eluent: ether/petroleum ether 57/43) m.p. 78° C. IR (nujol): 3290, 1740, 1695, 1630 cm$^{-1}$ $^1$H NMR (CDCl$_3$/TMS): 7.95 to 7.75 (m, 3H) 7.55 to 7.10 (m, 10H); 5.80 to 5.70 (m, 1H); 5.00 (s, 2H); 4.05 (s, 2H); 3.65 to 3.45 (m, 2H); 2.65 (t, 2H, J=6 Hz); 2.35 (s, 3H). Microanalysis: C$_{26}$H$_{25}$O$_4$NS Calc. % C=69.78 H=5.63 N=3.13 Found. % C=69.48 H=5.71 N=3.01

Example 36: Preparation of N-(E)-[1-oxo-2-(mercaptomethyl)-3-(1-naphthyl)propenyl]-β-alanine Saponification of the (E) diester obtained in Example 35 is carried out according to the experimental procedure described in Example 4. Yield: 39% m.p. 133° C. IR (nujol): 1735, 1620, 1575 cm$^{-1}$ $^1$H NMR (CDCl$_3$/TMS): 8.00 to 7.75 (m, 3H); 7.55 to 7.10 (m, 6H); 6.30 to 6.20 (m, 1H); 3.55 to 3.45 (m, 4H); 2.50 (t, 2H, J=6 Hz); 1.70 (t, 1H, J=8 Hz) Microanalysis: C$_{17}$H$_{17}$O$_3$NS Calc. % C=64.74 H=5.43 N=4.44 Found. % C=64.47 H=5.29 N=4.31

Example 37: Preparation of benzyl N-(Z)-[1-oxo-2-(acetylthiomethyl)-3-phenylpropenyl]-β-alaninate The (Z)-2-acetylthiomethyl-3-phenylpropenoic acid described in Example 1 (step B) is coupled with benzyl β-alaninate according to the experimental procedure described in Example 1 (step D). Yield: 78% (after recrystallization in ether) m.p. 80° C. IR: 3380, 1720, 1670, 1630, 1600 cm$^{-1}$ $^1$H NMR (CDCl$_3$): 7.60 (s, 1H); 7.45 to 7.15 (m, 10H); 6.90 (broad t, 1H); 5.15 (s, 2H); 3.95 (s, 2H); 3.65 (q. app., J:6.1 Hz); 2.65 (t, 2H, J=6.1 Hz); 2.35 (s, 3H). Microanalysis: C$_{22}$H$_{23}$NO$_4$S Calc. % C=60.48 H=5.83 N=3.52 Found. % C=66.29 H=5.78 N=3.51

Example 38: Preparation of N-(Z)-[1-oxo-2-(mercaptomethyl)-3-phenylpropenyl]-β-alanine 0.795 g (2.0 mmol) of the compound obtained in the above step, dissolved in 6 ml of methanol, is placed in a round-bottomed flask. The flask is flushed with argon and the solution is cooled in an ice bath. 5 ml of aqueous 1N sodium hydroxide solution is added at approximately 5° C. The mixture is stirred for 2 hours at 20° C. The methanol is evaporated off under vacuum at a temperature below 35° C. The basic aqueous phase is washed with ether (twice 10 ml). It is subsequently acidified with aqueous 1N HCl solution to pH 1. It is extracted with ether (twice 10 ml). The extraction phases are washed once with water, dried over MgSO$_4$, filtered and concentrated under vacuum. The residue is dried in a dessicator over phosphorus pentoxide in order to remove the acetic acid. It is purified by chromatography on silica (eluent: ether) Yield: 81% m.p. 132° C. IR: 3400, 1680, 1620, 1590 cm$^{-1}$ $^1$H NMR (acetone D6): 10.8 (broad s, 1H); 7.65 (broad t, 1H); 7.60 to 7.20 (m, 5H); 7.20 (s, 1H); 3.70 to 3.45 (m, 4H); 2.60 (t, 2H, J=6.7 Hz); 2.30 (t, 1H, J=5.9 Hz). Microanalysis: C$_{13}$H$_{15}$NO$_3$S Calc. % C=58.85 H=5.70 N=5.28 Found. % C=58.62 H=5.72 N=5.21

Example 39: Preparation of benzyl N-(Z)-[1-oxo-2-(acetylthiomethyl)-3-(4-phenoxyphenyl)propenyl]-β-alaninate

A) Preparation of (E)-2-methyl-3-(4-phenoxyphenyl)propenoic acid

The procedure is performed in an analogous manner to that described in Example 17 (step A), starting from 4-phenoxybenzaldehyde and using 5 equivalents of propionic anhydride. Yield: 68% IR (nujol): 1665 cm$^{-1}$ m.p. 133° C. $^1$H NMR (CDCl$_3$/TMS): 11.95 (broad s, 1H); 7.80 (s, 1H); 7.60 to 6.85 (m, 9H); 2.15 (s, 3H).

B) Preparation of (Z)-2-bromomethyl-3-(4-phenoxyphenyl)propenoic acid

The procedure is performed in an analogous manner to that described in Example 17 (step B). Yield: 76% m.p. 126° C. IR (nujol): 1670 cm$^{-1}$ $^1$H NMR (CDCl$_3$/TMS): 8.60 (broad s, 1H), 7.75 (s, 1H); 7.55 to 6.85 (m, 9H); 4.40 (s, 2H).

C) Preparation of (Z)-2-acetylthiomethyl-3-(4-phenoxyphenyl)propenoic acid

The procedure is performed in an analogous manner to that described in Example 17 (step C). Yield: 100% m.p. 118° C. IR (nujol): 1690, 1675, 1615 cm$^{-1}$ $^1$H NMR (CDCl$_3$/TMS): 10.30 (s, 1H); 7.80 (s, 1H); 7.55 to 6.85 (m, 9H); 3.80 (s, 2H); 2.30 (s, 3H).

D) Preparation of benzyl N-(Z)-[1-oxo-2-(acetylthiomethyl)-3-(4-phenoxyphenyl)propenyl]-β-alaninate The above (Z) acid is coupled with benzyl β-alaninate according to the experimental procedure described in Example 1 (step D). Yield: 66% (after flash chromatography, eluent: ethyl acetate/petroleum ether 30/70) m.p. 79° C. IR (nujol): 1730, 1690, 1645 cm$^{-1}$ $^1$H NMR (CDCl$_3$): 7.50 (s, 1H); 7.40 to 7.00 (m, 14H); 7.00 (t, 1H, J=6 Hz); 5.10 (s, 2H); 4.00 (s, 2H); 3.60 (q. app., 2H, J app.=7 Hz); 2.65 (t, 2H, J=6 Hz); 2.35 (s, 3H). $^{13}$C NMR (CDCl$_3$): 196.4; 172.4; 167.2; 158.3; 156.4; 138.0; 136.0; 131.4; 130.2; 129.7; 129.6; 128.9; 128.6; 128.5; 124.3; 119.9; 118.5; 66.7; 35.9; 34.2; 30.6; 26.8. Microanalysis: C$_{28}$H$_{27}$O$_5$NS Calc. % C=68.69 H=5.56 N=2.86 Found. % C=68.76 H=5.68 N=2.97

Example 40: Preparation of benzyl N-(E)-[1-oxo-2-(acetylthiomethyl)-3-(4-phenoxyphenyl)propenyl]-β-alaninate The procedure is performed in an analogous manner to that described in Example 18, starting from the (Z) isomer of Example 39 (step D).

Yield: 73% (after flash chromatography, eluent: ethyl acetate/petroleum ether 25/75). m.p. 88° C. IR (nujol): 1730, 1705, 1625 cm$^{-1}$ $^1$H NMR (CDCl$_3$): 7.30 to 6.90 (m, 14H); 6.70 (s, 1H); 6.10 (t, 1H, J=6 Hz); 5.00 (s, 2H); 3.80 (s, 2H); 3.50 (q. app., 2H, J app.=6 Hz); 2.50 (t, 2H, J=6 Hz); 2.30 (s, 3H). $^{13}$C NMR (CDCl$_3$): 194.9; 171.8; 168.4; 157.4; 156.4; 135.4; 133.2; 131.4; 130.0; 129.8; 129.7; 128.6; 128.3; 128.2; 123.6; 119.1; 118.3; 66.4; 34.6; 33.6; 33.3; 30.5. Microanalysis: C$_{28}$H$_{27}$O$_5$NS Calc. % C=68.69 H=5.56 N=2.86 Found. % C=68.72 H=5.58 N=2.79

Example 41: Preparation of N-(E)-[1-oxo-2-(mercaptomethyl)-3-(4-phenoxyphenyl)propenyl]-β-alanine Saponification of the (E) diester obtained in Example 40 is carried out according to the experimental procedure described in Example 4. Yield: 55% m.p. 108° C. $^1$H NMR (CDCl$_3$): 9.60 (broad s, H); 7.30 to 6.80 (m, 9H); 6.50 (s, 1H); 6.30 (t, 1H, J=6 Hz); 3.50 to 3.40 (m, 4H); 2.50 (t, 2H, J=6 Hz); 1.70 (t, 1H, J=8 Hz). IR (nujol): 3290, 1725, 1660, 1650 cm$^{-1}$ Microanalysis: C$_{19}$H$_{19}$NSO$_4$ Calc. % C=63.85

H=5.38 N=3.92 Found. % C=63.66 H=5.14 N=3.69

Example 42: Preparation of benzyl N-(Z)-[1-oxo-2-(acetylthiomethyl)-3-(3,4-methylenedioxyphenyl)propenyl]-β-alaninate

A) Preparation of (E)-2-methyl-3-(3,4-methylenedioxyphenyl)propenoic acid

The procedure is performed in an analogous manner to that described in Example 17 (step A), starting from piperonal. Yield: 65% m.p. 205° C. $^1$H NMR (DMSOd$_6$): 10.1 (broad s, 1H); 7.50 (s, 1H); 7.00 (s, 1H); 6.95 (s, 2H); 6.05 (s, 2H); 2.00 (s, 3H).

B) Preparation of (Z)-2-bromomethyl-3-(3,4-methylenedioxyphenyl)propenoic acid The procedure is performed in an analogous manner to that described in Example 17 (step B). Yield: 75% m.p. 158° C. $^1$H NMR (CDCl$_3$/TMS): 8.60 (s, 1H); 7.70 (s, 1H); 7.30 to 6.70 (m, 3H); 6.00 (s, 2H); 4.35 (s, 2H).

C) Preparation of (Z)-2-acetylthiomethyl-3-(3,4-methylenedioxyphenyl)propenoic acid The procedure is performed in an analogous manner to that described in Example 17 (step. C). Yield: 86% m.p. 142° C. $^1$H NMR (CDCl$_3$/TMS): 8.60 (s, 1H); 7.80 (s, 1H); 7.10 to 6.70 (m, 3H); 6.00 (s, 2H); 4.05 (s, 2H); 2.30 (s, 3H).

D) Preparation of benzyl N-(Z)-[1-oxo-2-(acetylthiomethyl)-3-(3,4-methylenedioxyphenyl)propenyl]-β-alaninate The above (Z) acid is coupled with benzyl β-alaninate according to the experimental procedure described in Example 1 (step D). Yield: 61% (after flash chromatography, eluent: ether/petroleum ether 50/50). m.p. 76° C. IR (nujol); 1730, 1705, 1620 cm$^{-1}$ $^1$H NMR (CDCl$_3$): 7.55 (s, 1H), 7.35 (s, 5H); 6.90 (broad s, 1H); 6.80 (broad s, 3H); 6.00 (s, 2H); 5.20 (s, 2H); 4.00 (s, 2H); 3.65 (q. app., 2H, J. app=7 Hz); 2.70 (t, 2H, J=6 Hz); 2.35 (s, 3H). Microanalysis: C$_{23}$H$_{23}$O$_6$NS Calc. % C=62.57 H=5.25 N=3.17 Found. % C=62.76 H=5.48 N=3.23

Example 43: Preparation of benzyl N-(E)-[1oxo-2-(acetylthiomethyl)-3-(3,4-methylenedioxyphenyl)propenyl]-β-alaninate The procedure is performed in an analogous manner to that described in Example 18, starting from the (Z) isomer of Example 42 (step D). Yield: 73% (after flash chromatography, eluent: ether/petroleum ether 55/45). m.p. 84° C. IR (nujol): 1735, 1695 cm$^{-1}$ $^1$H NMR (CDCl$_3$): 7.30 (broad s, 5H); 6.95 to 6.80 (m, 4H); 6.20 (m, 1H); 5.90 (s, 2H); 5.10 (s, 2H); 3.85 (s, 2H); 3.50 (q. app., 2H, J app.=6 Hz); 2.50 (t, 2H, J=6 Hz); 2.30 (s, 3H). Microanalysis: C$_{23}$H$_{23O6}$NS Calc. % C=62.57 H=5.25 N=3.17 Found. % C=62.48 H=5.06 N=3.25

The results of the biological studies, presented below, demonstrate the enkephalinase-inhibitory properties of the compounds of formula (Ia) and (Ib) in accordance with the invention.

The present invention thus also relates to the pharmaceutical compositions which contain, as active principle, the compounds of formula (Ia) or (Ib) in accordance with the invention in therapeutically effective amounts.

BIOLOGICAL STUDY

An assay of the enkephalinase-inhibitory activity (J. Pharmac. Exp. Ther., 1987, 243, 666) of the compounds of formulae (Ia) and (Ib) was performed.

The results obtained are presented in the table which follows:

IN VITRO BIOLOGICAL RESULTS ON ENKEPHALINASE

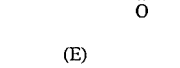

| $R_1$ | AA | (E) Isomer IC$_{50}$ (nM) | | (Z) Isomer IC$_{50}$ (nM) | |
|---|---|---|---|---|---|
| Ph | HN–COOH | Ex 4 | 2.8 | Ex 38 | 171.0 |
| | HN–COOH (branched) | Ex 12 | 7.0 | | |
| | HN–COOH | Ex 14 | 10.0 | | |
| | HN–COOH | Ex 16 | 6.4 | | |
| 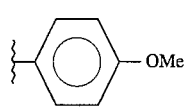 –OMe | HN–COOH | Ex 19 | 2.7 | Ex 17* | 97.0 |

IN VITRO BIOLOGICAL RESULTS ON ENKEPHALINASE $$\text{(E)} \quad \underset{\text{HS}}{\overset{R_1}{\diagup}}\!\!\!\diagdown\!\!\text{AA} \qquad \text{(Z)} \quad \underset{\text{HS}}{\overset{R_1}{\diagdown}}\!\!\!\diagup\!\!\text{AA}$$

| $R_1$ | AA | (E) Isomer IC$_{50}$ (nM) | | (Z) Isomer IC$_{50}$ (nM) | |
|---|---|---|---|---|---|
| 4-CF$_3$-C$_6$H$_4$- | HN-CH$_2$-CH$_2$-COOH | Ex 22 | 12.1 | | |
| 4-Ph-C$_6$H$_4$- | HN-CH$_2$-CH$_2$-COOH | Ex 25 | 7.5 | Ex 23* | 65.0 |
| 4-OEt-C$_6$H$_4$- | HN-CH$_2$-CH$_2$-COOH | Ex 28 | 11.8 | Ex 26* | 0% at 0.3 µM |
| 4-OPr-C$_6$H$_4$- | NH-CH$_2$-CH$_2$-COOH | Ex 30* | 0% at 0.3 µM | | |
| 2,4-diF-C$_6$H$_3$- | HN-CH$_2$-CH$_2$-COOH | Ex 33 | 5.9 | Ex 31* | 16% at 0.3 µM |
| 4-(OCH$_2$Ph)-C$_6$H$_4$- | HN-CH$_2$-CH$_2$-COOH | Ex 41 | 5.8 | | |
| 3,4-methylenedioxy-C$_6$H$_3$- | HN-CH$_2$-CH$_2$-COOH | Ex 43 | 19 | Ex 42* | 0% at 0.3 µM |

*by enzymatic deprotection of the diester

These results illustrate the advantageous enkephalinase-inhibitory-properties of the compounds according to the invention, which make themuseful in human and veterinary medicine.

The pharmaceutical compositions which contain the compounds of formula (Ia) or (Ib) according to the invention are useful in the indications resulting from the central properties, in particular as painkillers, and the peripheral properties, in particular as anti-diarrhoea agents, of the enkephalinase inhibitors, as well as in the indications of ANF protectors, in particular arterial hypertension and cardiac insufficiency.

The pharmaceutical compositions which contain, as active principle, the compounds of formula (Ia) or (Ib) in accordance with the invention may be administered to man via the oral, parenteral or rectal route.

These pharmaceutical compositions may be in solid or liquid form and may be provided in the pharmaceutical forms commonly used in human medicine, such as, for example, in the form of simple or coated tablets, gelatin capsules, suppositories or injectable preparations.

The pharmaceutical compositions in accordance with the invention may be administered in unit doses, preferably of 20 to 200 mg of active principle.

We claim:
1. Amino acid derivatives, characterized in that they correspond to the general formulae

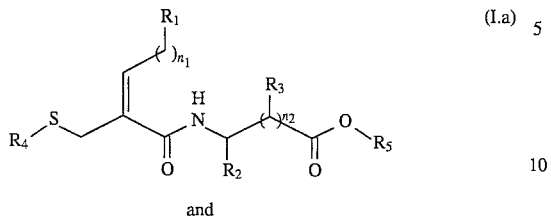 (I.a)

and

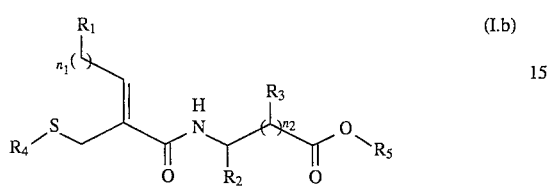 (I.b)

in which $R_1$ represents a hydrogen atom, a phenyl group which is optionally mono- or polysubstituted with a halogen atom, a trifluoromethyl group, a nitro group, a cyano group or an amino group, a lower alkyl group or a lower phenylalkylene group; the group

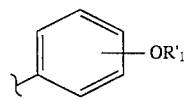

where $R'_1$ represents a hydrogen atom, a lower alkyl group, a phenyl group or a lower phenylalkylene group; a group

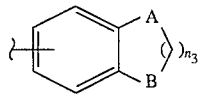

where A, B and $n_3$ have the meanings given below

| A | B | $n_3$ |
|---|---|---|
| O | O | 1 |
| O | $CH_2$ | 1 |
| $CH_2$ | $CH_2$ | 1 |
| O | O | 2 |
| $CH_2$ | $CH_2$ | 2 |
| O | $CH_2$ | 2 | a biphenyl group, alpha and beta naphthyl, $n_1$ varies from 0 to 10

$n_2$ varies from 1 to 10

$R_2$ represents a hydrogen atom; a lower alkyl group; a lower hydroxyalkylene group; a phenyl group; a lower phenylalkylene group; a lower hydroxyphenylalkylene group; a lower aminoalkylene group; a lower guanidinoalkylene group; a lower mercaptoalkylene group; a lower thioalkylene lower alkyl group; a lower imidazolylalkylene group; a lower indolylalkylene group; a lower carbamylalkylene group; a lower carboxyalkylene group;

$R_3$ also represents a hydrogen atom or one of the groups mentioned above for the definition of $R_2$;

$R_4$ represents a hydrogen atom, a linear or branched aliphatic acyl radical, an aromatic acyl radical which is optionally mono- or polysubstituted, or a linear or branched acyl radical containing one or more oxygen atoms;

$R_5$ represents a hydrogen atom; a linear or branched lower alkyl group; a phenyl group or a lower phenylalkylene group, the two last-mentioned groups being optionally mono- or polysubstituted on the phenyl ring; a linear or branched substituent containing one or more oxygen atoms.

2. Amino acid derivatives according to claim 1, characterized in that $R_1$ represents a phenyl group which is optionally mono- or polysubstituted with a halogen atom or with the trifluoromethyl group; the group

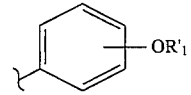

where $R'_1$ represents a lower alkyl group, a phenyl group; the group

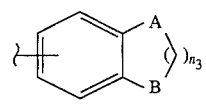

where A and B represent oxygen and $n_3$ is equal to 1 or 2; a biphenyl group, alpha and beta naphthyl;

$R_2$ and $R_3$ represent a hydrogen atom or a lower alkyl radical;

$R_4$ represents a hydrogen atom, a linear or branched aliphatic acyl radical or an aromatic acyl radical;

$R_5$ represents a hydrogen atom, a lower alkyl radical or a phenyl radical;

$n_1$ is equal to 0 or 1;

$n_2$ is equal to 1 or 2.

3. Amino acid derivatives according to claim 1, characterized in that they are chosen from:

benzyl N-(E)-[1-oxo-2-(acetylthiomethyl)-3-phenylpropenyl]-β-alaninate, methyl N-(E)-[1-oxo-2-(acetylthiomethyl)-3-phenylpropenyl]-β-alaninate, ethyl N-(E)-[1-oxo-2-(acetylthiomethyl)-3-phenylpropenyl]-β-alaninate, N-(E)-[1-oxo-2-(mercaptomethyl)-3-phenylpropenyl]-β-alanine, benzyl N-(E)-[1-oxo-2-(benzoylthiomethyl)-3-phenylpropenyl]-β-alaninate, methyl N-(E)-[1-oxo-2-(benzoylthiomethyl)-3-phenylpropenyl]-β-alaninate, ethyl N-(E)-[1-oxo-2-(benzoylthiomethyl)-3phenylpropenyl]-β-alaninate, benzyl N-(E)-[1-oxo-2-(pivaloylthiomethyl)-3-phenylpropenyl]-β-alaninate, methyl N-(E)-[1-oxo-2-(pivaloylthiomethyl)-3-phenylpropenyl]-β-alaninate, ethyl N-(E)-[1-oxo-2-(pivaloylthiomethyl)-3-phenylpropenyl]-β-alaninate, methyl 3-(RS)-N-(E)-[1-oxo-2-(acetylthiomethyl)-3-phenylpropenyl]aminobutanoate, 3-(RS)-N-(E)-[1-oxo-2-(mercaptomethyl)-3-phenylpropenyl]aminobutanoic acid, methyl 3-(RS)-N-(E)-[1-oxo-2-(acetylthiomethyl)-3-phenylpropenyl]amino-2-methylpropanoate, 3-(RS)-N-(E)-[1-oxo-2-(mercaptomethyl)-3-phenylpropenyl]amino-2-methylpropanoic acid, benzyl 4-N-(E)-[1-oxo-2-(acetylthiomethyl)-3-phenylpropenyl]aminobutanoate, 4-N-(E)-[1-oxo-2-(mercaptomethyl)-3-phenylpropenyl]aminobutanoic acid, benzyl N-(Z)-[1-oxo-2-(acetylthiomethyl)-3-(4-methoxyphenyl)propenyl]-β-alaninate, benzyl N-(E)-[1-oxo-2-(acetylthiomethyl)-3-(4-methoxyphenyl)propenyl]-β-alaninate, N-(E)-[1-oxo-2-(mercaptomethyl)-3-(4-methoxyphenyl)propenyl]-β-alanine, benzyl N-(Z)-[1-oxo-2-(acetylthiomethyl)-3-(4-trifluoromethylphenyl)propenyl]-β-alaninate, benzyl N-(E)-[1-oxo-2-(acetylthiomethyl)-3-(4-trifluoromethylphenyl)propenyl]-β-alaninate, N-(E)-[1-oxo-2-(mercaptomethyl)-3-(4-trifluoromethylphenyl)propenyl]-β-alanine, benzyl N-(Z)-[1-oxo-2-(acetylthiomethyl)-3-(4-phenylphenyl)propenyl]-β-alaninate, benzyl N-(E)-[1-oxo-2-(acetylthiomethyl)-3-(4-phenylphenyl)propenyl]-β-alaninate, N-(E)-[1-oxo-2-(mercaptomethyl)-3-(4-phenylphenyl)propenyl]-β-alanine, benzyl N-(Z)-[1-oxo-2-(acetylthiomethyl)-3-(4-ethoxyphenyl)propenyl]-β-alaninate, benzyl N-(E)-[1-oxo-2-(acetylthiomethyl)-3-(4-ethoxyphenyl)propenyl]-β-alaninate, N-(E)-[1-oxo-2-(mercaptomethyl)-3-(4-ethoxyphenyl)propenyl]-β-alanine, benzyl N-(Z)-[1-oxo-2-(acetylthiomethyl)-3-(4-propoxyphenyl)propenyl]-β-alaninate, benzyl N-(E)-[1-oxo-2-(acetylthiomethyl)-3-(4-propoxyphenyl)propenyl]-β-alaninate, benzyl N-(Z)-[1-oxo-2-(acetylthiomethyl)-3-(3,5-difluorophenyl)propenyl]-β-alaninate, benzyl N-(E)-[1-oxo-2-(acetylthiomethyl)-3-(3,5-difluorophenyl)propenyl]-β-alaninate, N-(E)-[1-oxo-2-(mercaptomethyl)-3-(3,5-difluorophenyl)propenyl]-β-alanine, benzyl N-(Z)-[1-oxo-2-(acetylthiomethyl)-3-(1naphthyl)propenyl]-β-alaninate, benzyl N-(E)-[1-oxo-2-(acetylthiomethyl)-3-(1naphthyl)propenyl]-β-alaninate, N-(E)-[1-oxo-2-(mercaptomethyl)-3-(1-naphthyl)propenyl]-β-alanine, benzyl N-(Z)-[1-oxo-2-(acetylthiomethyl)-3(phenyl)propenyl]-β-alaninate, N-(Z)-[1-oxo-2-(mercaptomethyl)-3-(phenyl)propenyl]-β-alanine, benzyl N-(Z)-[1-oxo-2-(acetylthiomethyl)-3-(4-phenoxyphenyl)propenyl]-β-alaninate, benzyl N-(E)-[1-oxo-2-(acetylthiomethyl)-3-(4-phenoxyphenyl)propenyl]-β-alaninate, N-(E)-[1-oxo-2-(mercaptomethyl)-3-(4-phenoxyphenyl)propenyl]-β-alanine, benzyl N-(Z)-[1-oxo-2-(acetylthiomethyl)-3-(3,4-methylenedioxyphenyl)propenyl]-β-alaninate, benzyl N-(E)-[1-oxo-2-(acetylthiomethyl)-3-(3,4-methylenedioxyphenyl)propenyl]-β-alaninate.

4. Medicament exhibiting an enkephalinase-inhibitory activity, characterized in that it contains, as active principle, a compound according to claim 1.

5. Medicament according to claim 4, characterized in that it is provided in the form of unit doses containing from 20 to 200 mg of active principle.

\* \* \* \* \*